(12) United States Patent
Nagai et al.

(10) Patent No.: US 8,658,630 B2
(45) Date of Patent: *Feb. 25, 2014

(54) ALLERGEN DEPRESSANT AND DEPRESSION METHOD

(75) Inventors: Satoshi Nagai, Wakayama (JP); Katsuyuki Takano, Wakayama (JP); Masahiro Suzuki, Wakayama (JP); Takeshi Ban, Sumida-ku (JP); Michio Yokosuka, Chuo-ku (JP); Takeshi Ihara, Wakayama (JP); Tohru Nishioka, Wakayama (JP)

(73) Assignee: Kao Corporation, Tokyo (JP)

( * ) Notice: Subject to any disclaimer, the term of this patent is extended or adjusted under 35 U.S.C. 154(b) by 257 days.

This patent is subject to a terminal disclaimer.

(21) Appl. No.: 12/696,835

(22) Filed: Jan. 29, 2010

(65) Prior Publication Data

US 2010/0126525 A1    May 27, 2010

Related U.S. Application Data

(62) Division of application No. 10/576,948, filed as application No. PCT/JP2004/015877 on Oct. 20, 2004, now abandoned.

(30) Foreign Application Priority Data

| Oct. 22, 2003 | (JP) | 2003-361994 |
| Jul. 14, 2004 | (JP) | 2004-207278 |
| Jul. 14, 2004 | (JP) | 2004-207279 |
| Jul. 14, 2004 | (JP) | 2004-207280 |

(51) Int. Cl.
| *A61K 31/56* | (2006.01) |
| *A61K 31/075* | (2006.01) |
| *A61K 31/765* | (2006.01) |

(52) U.S. Cl.
USPC .................. 514/182; 514/715; 424/78.37

(58) Field of Classification Search
None
See application file for complete search history.

(56) References Cited

U.S. PATENT DOCUMENTS

| 4,939,192 | A | 7/1990 | t'Sas |
| 5,104,646 | A | 4/1992 | Bolich et al. |
| 5,106,609 | A | 4/1992 | Bolich et al. |
| 6,395,269 | B1 | 5/2002 | Fuller et al. |
| 6,541,614 | B1 | 4/2003 | Nagasawa et al. |
| 7,262,158 | B1 | 8/2007 | Lukenbach et al. |
| 8,133,991 | B2 * | 3/2012 | Nonomura et al. |
| 2002/0035046 | A1 | 3/2002 | Lukenbach et al. |
| 2002/0193437 | A1 * | 12/2002 | Nagatsuka et al. |
| 2005/0256082 | A1 * | 11/2005 | Nonomura et al. |

FOREIGN PATENT DOCUMENTS

| EP | 1 191 039 A1 | 3/2002 |
| GB | 2 300 122 | 10/1996 |
| JP | 56-049080 | 5/1981 |
| JP | 2000-504621 | 4/2000 |
| JP | 2000-264837 | 9/2000 |
| JP | 2002-508438 | 3/2002 |
| JP | 2002-128659 | 5/2002 |
| JP | 2002-128680 | 5/2002 |
| WO | 98/29528 | 7/1998 |
| WO | 99/07220 | 2/1999 |
| WO | 99/31211 | 6/1999 |
| WO | 00/73351 | 12/2000 |
| WO | 02/28179 | 4/2002 |

OTHER PUBLICATIONS

Nishioka et al., Journal of Allergy and Clinical Immunology, 1998, vol. 101(1), Part 1, pp. 28-32.*
The Merck Index—An Encyclopedia of Chemicals, Drugs, and Biologicals, 14th Edition, Online version, O'Neil, Maryadele J. et al., (2006, 2012), "1,3-Butylene Glycol", downloaded from "http://www.knovel.com/web/portal/browse/display?_EXT_KNOVEL_DISPLAY_bookid=1863&VerticalID=0" on Apr. 4, 2012, pp. 1-2 of 2.*
Rohm and Haas, "Aculyn™ 22 Rheology Modifier/Stabilizer" Product Bulletin, published by Rohm and Haas, Sep. 2002 pp. 1-13.

* cited by examiner

*Primary Examiner* — Savitha Rao
*Assistant Examiner* — Gregg Polansky
(74) *Attorney, Agent, or Firm* — Oblon, Spivak, McClelland, Maier & Neustadt, L.L.P.

(57) ABSTRACT

The invention provides a means capable of effectively inactivating and removing allergen or a precursor thereof. The invention relates to an allergen-reducing agent containing water and a water-soluble polymer compound having units having hydroxy or carboxy groups wherein at least a part of hydrogen atoms of the hydroxy or carboxy groups are substituted by specific groups containing a polyether group.

15 Claims, No Drawings

US 8,658,630 B2

ALLERGEN DEPRESSANT AND DEPRESSION METHOD

TECHNICAL FIELD

The present invention relates to a method of easily removing allergen or its precursor floating in housing space and an allergen-reducing agent used for the method.

FIELD OF THE INVENTION

Allergic diseases attributable to house dust tend to increase in recent years and become a social problem. Typical examples of house dust causing allergy can include pollen, mold spores, and dead bodies and excrements of mites, but these are very fine substances of several to tens μm and can thus be stirred up even by simple activity such as human walking to contaminate housing space. The house dust stirred up to float in the space cannot be removed by general cleaning action, so there is an ardent desire for a method of effectively removing house dust floating in space. JP-A 2000-264837 discloses an allergen removing agent as a cationic surfactant-containing composition to be sprayed into space. JP-A 2002-128659 discloses a house dust-treating agent sprayed into space to inactivate and/or remove allergen. JP-A 2002-128680 discloses a house dust-treating agent as a polyvinyl alcohol-containing solution to be sprayed into space. JP-A 2000-504621 discloses a method of removing a floating particulate substance in a household environment. WP-A 02/28179 discloses a composition for making allergen harmless for the case where the amount of dust remaining in fibers is 30% or more in a dust control test and the MIU value by a method of analyzing frictional coefficient is 3.0 or less, and as a specific compound, a polymer compound is described therein. GB-B 2300122 describes a technique of controlling allergen, which includes using a water-soluble polysaccharide such as hydroxypropyl cellulose to allow small mite allergen to adhere to the surface thereof so as to stabilize the allergen. JP-A 2002-508438 describes a domestic composition containing a vehicle and a household ingredient, said vehicle including a hydrophobic modified water-soluble polysaccharide polymer containing both a water-soluble polysaccharide polymer main chain and a hydrophobic moiety. WO-A 00/73351 discloses a novel polysaccharide derivative as a compound having an action of stabilizing a hydrophobic substance, wherein a hydrogen atom of a hydroxy group of the polysaccharide is substituted by a group containing a specific polyoxyalkylene group.

SUMMARY OF THE INVENTION

The present invention relates to an allergen-reducing agent containing water and a water-soluble polymer compound having units having hydroxy or carboxy groups wherein at least a part of hydrogen atoms of the hydroxy or carboxy groups are substituted by groups represented by the following formula (1):

wherein $R^{1a}$ is a C1 to C6 alkylene group which may be substituted with a hydroxy or oxo group, $R^{1b}$ is a C1 to C6 alkylene group, $R^{1c}$ is a group selected from a C4 to C30 hydrocarbon group which may be substituted with a hydroxy group, a C1 to C5 sulfoalkyl group which may be substituted with a hydroxy group, and a hydrocarbon group which has a steroid skeleton, A is a group selected from —O—, —OCO— and —COO—, p is 0 to 50 (average number of moles added), and $(OR^{1b})$ moles whose number is p may be the same or different.

The present invention also relates to an allergen-reducing agent contained in a spray container, which contains the allergen-reducing agent of the present invention introduced into a container provided with a spray device.

The present invention also relates to an allergen-reducing sheet containing a flexible sheet impregnated with the allergen-reducing agent of the present invention.

The present invention also relates to a method of reducing allergen, which includes spraying the allergen-reducing agent of the present invention into space.

Further, the present invention relates to a method of reducing allergen, which includes spraying or applying the allergen-reducing agent of the present invention onto the surface of an object, and before drying, wiping it away with a water-absorbing article, as well as a cleaning method which includes carrying out said method and subsequent cleaning by vacuuming or sweeping cleaning.

Furthermore, the present invention relates to a cleaning method which includes wiping the surface of an object with an allergen-reducing sheet having a flexible sheet impregnated with the allergen-reducing agent of the present invention and subsequent cleaning by vacuuming or sweeping cleaning.

DETAILED DESCRIPTION OF THE INVENTION

The inactivation and removal of allergic substances cannot be sufficiently effected even by the means described in the above literatures.

The object of the present invention is to provide an agent and method capable of effectively inactivating and removing allergen or a precursor thereof.

The allergen-reducing agent according to the present invention contains a water-soluble polymer compound (hereinafter, ref erred to as component (a)) having units having hydroxy or carboxy groups, which is composed in particular of such units as a main chain wherein a part or the whole of hydrogen atoms of the hydroxy or carboxy groups are substituted by groups represented by the formula (1) below. In the present invention, the water solubility of the water-soluble polymer compound in the present invention refers to a solubility of 1 wt % or more in water at 20° C.

wherein $R^{1a}$ is a C1 to C6 alkylene group which may be substituted with a hydroxy or oxo group, $R^{1b}$ is a C1 to C6 alkylene group, $R^{1c}$ is a group selected from a C4 to C30 hydrocarbon group which may be substituted with a hydroxy group, a C1 to C5 sulfoalkyl group which may be substituted with a hydroxy group, and a hydrocarbon group which has a steroid skeleton, A is a group selected from —O—, —OCO— and —COO—, p is 0 to 50 (average number of moles added), and $(OR^{1b})$ moles whose number is p may be the same or different.

$R^{1a}$ is preferably an ethylene group, propylene group, trimethylene group, 2-hydroxytrimethylene group, 1-hydroxytrimethylene group, 1-oxoethylene group, 1-oxotrimethylene group or 1-methyl-2-oxoethylene group, particularly preferably a 2-hydroxytrimethylene group or 1-hydroxytrimethylene group. $R^{1b}$ is preferably an ethylene group or propylene group, $R^{1c}$ is a linear or branched alkyl or alkenyl group or a C4 to C30 hydrocarbon group such as a hydrocarbon group (preferably a cholesteryl group) having a steroid skeleton, preferably a C5 to C25, more preferably C6 to C20, alkyl group which may be substituted with a hydroxy group, or a 2-sulfoethyl group, 3-sulfopropyl group, 3-sulfo-2-hydroxypropyl group or 2-sulfo-1-(hydroxymethyl)ethyl group. A is preferably —O—, p is preferably a number of 0 to 40, more preferably 0 to 30, even more preferably 0 to 20, even more preferably 10 to 20 (average number of moles added).

The water-soluble polymer serving as the component (a) includes polysaccharides such as cellulose, starch, guar gum, xanthane gum, pullulan, dextran, cluster dextrin, fructan, mannan, agar, carrageenan, chitin, chitosan, pectin, alginic acid, hyaluronic acid, inulin etc.; and derivatives thereof substituted with a methyl group, ethyl group, hydroxyethyl group, hydroxypropyl group etc. Its constituent monosaccharide residue may be substituted with one or more of these substituent groups. Examples of the polysaccharide derivatives include hydroxyethyl cellulose, hydroxyethylethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, hydroxypropylmethyl starch etc. These polysaccharides or derivatives thereof are preferably cellulose, starch, hydroxyethyl cellulose, methyl cellulose, ethyl cellulose, hydroxypropyl cellulose, inulin, chitosan, cluster dextrin and guar gum, particularly preferably hydroxyethyl cellulose, inulin, chitosan, cluster dextrin and guar gum. The substituent group of the polysaccharide derivative can further be substituted with a hydroxy group such as a hydroxyethyl group or hydroxypropyl group to form, for example, a polyoxyethylene chain or the like thereby attaining a substitution degree of 3.0 or more per constituent monosaccharide residue, and the substitution degree per constituent monosaccharide residue is preferably 0.1 to 10.0, more preferably 0.5 to 5.0.

In the present invention, the component (a) is a polymer compound wherein a part or the whole of hydrogen atoms of hydroxy groups or carboxy groups in the water-soluble polymer described above are substituted by the substituent groups of the formula (1), and the degree of substitution with the substituent group (1) is preferably in the range of 0.0001 to 1, more preferably 0.0005 to 0.5, even more preferably 0.001 to 0.1, even more preferably 0.001 to 0.05, per monomer unit residue containing a hydroxy or carboxy group (for example, per constituent monosaccharide residue). When $R^{1c}$ in the formula (1) is a sulfoalkyl group, the degree of substitution on the sulfoalkyl group is preferably in the range of 0 to 1, more preferably 0 to 0.8, even more preferably 0 to 0.5, per monomer unit residue containing a hydroxy or carboxy group (for example, per constituent monosaccharide residue).

The number-average molecular weight of the component (a) is preferably 10,000 to 2,000,000, more preferably 50,000 to 1,500,000, even more preferably 100,000 to 600,000. The weight-average molecular weight can be determined by gel permeation chromatography (GPC) with polyethylene glycol as standard.

The weight-average molecular weight of the component (a) can be determined by high performance anion exchange chromatography (HPAEC) with a pulse amperometric detector, or by capillary electrophoresis.

Some components (a) in the present invention can be obtained according to a method described in WO00/73351 by reacting a cellulose derivative or a starch derivative with a compound represented by $R^{1d}$—$(OR^{1b})_p$-A-$R^{1c}$ wherein $R^{1d}$ represents a C3 to C6 epoxylated alkyl group, a C1 to C6 halogenated alkyl group which may be substituted with a hydroxy group, a carboxy group or a C2 to C6 carboxyalkyl group, or a derivative thereof, and $R^{1b}$, p, A and $R^{1c}$ each have the same meaning as defined above, if desired, followed by sulfonation with a usual sulfonating agent.

Another water-soluble polymer compound serving as the component (a) includes a polymer compound obtained from a monomer capable of forming a unit having a hydroxy or carboxy group, such as acrylic acid, vinyl acetate (production of polyvinyl alcohol) and glycidol, wherein the hydroxy or carboxy group of the polymer compound is substituted with the group of the formula (1) above.

In the present invention, the component (a) is preferably the following polymer compound (A) or (B):
(A): a water-soluble polymer compound containing a monomer unit (a1) of the following formula (2) and a monomer unit (a2) of the following formula (3) wherein the molar ratio of (a1)/(a2) is 1/1500 to 30/100, and the proportion of (a1) and (a2) in total in the molecule is 50 to 100 mol % (hereinafter, referred to as polymer compound (A)).

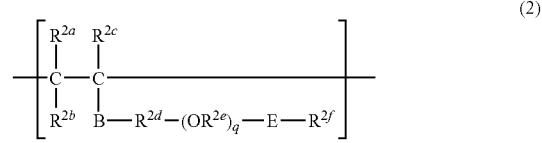

wherein $R^{2a}$ is a hydrogen atom or a C1 to C3 alkyl group, $R^{2b}$ is a group selected from a hydrogen atom and —COOM (whereupon M is a hydrogen atom, an alkali metal atom or an alkaline earth metal atom), $R^{2c}$ is a group selected from a hydrogen atom, a C1 to C3 alkyl group and a hydroxy group, $R^{2d}$ is a C1 to C6 alkylene group which may be substituted with a hydroxy group, $R^{2e}$ is a C1 to C6 alkylene group, $R^{2f}$ is a C4 to C30 hydrocarbon group which may be substituted with a hydroxy group, B is a group selected from —O—, —COO—, —OCO— and —CONR$^{2g}$— (whereupon $R^{2g}$ is a hydrogen atom, a C1 to C3 alkyl group or a C1 to C3 hydroxyalkyl group), and E is a group selected from —O—, —OCO— and —COO—, and q is 0 to 50 (average number of moles added), and ($OR^{2e}$) moles whose number is q may be the same or different; and

wherein $R^{3a}$ is a hydrogen atom or a C1 to C3 alkyl group, $R^{3b}$ is a group selected from a hydrogen atom and —COOM (whereupon M is a hydrogen atom, an alkali metal atom or an alkaline earth metal atom), $R^{3c}$ is a group selected from a hydrogen atom, a C1 to C3 alkyl group and a hydroxy group, G is —COOM, —OH, -T-($R^{3d}$O)$_c$—H, —CON($R^{3e}$)($R^{3f}$), —COO—$R^{3g}$—N$^+$($R^{3h}$)($R^{3i}$)($R^{3j}$).X$^-$, —COO—$R^{3g}$—N($R^{3h}$)($R^{3i}$), —CON($R^{3e}$)—$R^{3g}$—N$^+$($R^{3h}$)($R^{3i}$)($R^{3j}$).X$^-$, —CON($R^{3e}$)—$R^{3g}$—N($R^{3h}$)($R^{3i}$), or a 5- or 6-membered heterocyclic group having at least one amino or amide group in the ring, wherein M is a hydrogen atom, an alkaline metal atom or an alkaline earth metal atom, and T is a group selected from —O— and —COO—, $R^{3d}$ is a C1 to C6 alkylene group, $R^{3e}$, $R^{3f}$, $R^{3h}$, $R^{3i}$ and $R^{3j}$ each represent a hydrogen atom, a C1 to C3 alkyl group or a C1 to C3 hydroxyalkyl group, $R^{3g}$ is a C1 to C5 alkylene group, $X^-$ represents an organic or inorganic anion group, and c is 1 to 50 (average number of moles added), and $(R^{3d}O)$ moles whose number is c may be the same or different.

(B): a polymer compound containing a monomer unit (a3) of the following formula (4) and/or the following formula (5) and a monomer unit (a4) of the following formula (6) and/or the following formula (7) wherein the molar ratio of (a4)/(a3) is 30/100 to 1/1500, and the proportion of (a4) and (a3) in total in the molecule is 50 to 100 mol % (hereinafter, referred to as polymer compound (B)).

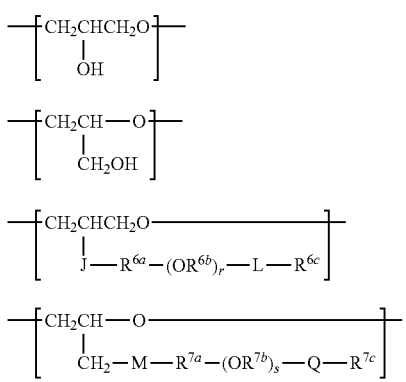

(4)

(5)

(6)

(7)

wherein each of J and M is a group selected from —O—, —OCO— and —COO—, each of $R^{6a}$ and $R^{7a}$ is a C1 to C6 alkylene group, each of $R^{6b}$ and $R^{7b}$ is a C1 to C6 alkylene group, each of $R^{6c}$ and $R^{7c}$ is a C4 to C30 hydrocarbon group which may be substituted with a hydroxy group, each of L and Q is a group selected from —O—, —OCO— and —COO—, and each of r and s is 0 to 50 (average number of moles added), and $(OR^{6b})$ moles whose number is r or $(OR^{7b})$ moles whose number is s may be the same or different.

<Polymer Compound (A)>

In the formula (2), each of $R^{2a}$ and $R^{2b}$ is preferably a hydrogen atom, and $R^{2c}$ is preferably a hydrogen atom or a methyl group. $R^{2f}$ is preferably a C10 to C24 alkyl or alkenyl group, more preferably a C10 to C18 alkyl group. B is preferably —O—, —COO— or —CONR$^{2g}$— wherein $R^{2g}$ is preferably a hydrogen atom. $R^{2d}$ is a group selected from an ethylene group, a propylene group or —CH$_2$CH(OH)CH$_2$—, and $R^{2e}$ is a group selected from an ethylene group, a propylene group or —CH$_2$CH(OH)CH$_2$—, preferably an ethylene group. E is preferably —O—, and q is preferably a number of 0 to 40, more preferably 0 to 30, even more preferably 0 to 20, even more preferably 10 to 20 (average number of moles added).

In the formula (3), each of $R^{3a}$ and $R^{3b}$ is preferably a hydrogen atom, $R^{3c}$ is preferably a hydrogen atom or a methyl group. Each of $R^{3e}$, $R^{3f}$, $R^{3h}$, $R^{3i}$ and $R^{3j}$ is preferably a hydrogen atom, methyl group, ethyl group or hydroxyethyl group, and particularly each of $R^{3f}$, $R^{3h}R^{3i}$ and $R^{3j}$ is even more preferably a methyl group, and $R^{3e}$ is even more preferably a hydrogen atom or a methyl group. $R^{3g}$ is preferably an ethylene group or a propylene group. The heterocyclic group can include a pyrrolidone group, pyridine group and imidazole group, among which a pyrrolidone group is preferable. $X^-$ is a chlorine ion, sulfate ion, C1 to C3 alkyl sulfate ion, C1 to C12 fatty acid ion, benzenesulfonate ion which may be substituted with one to three C1 to C3 alkyl groups, and is preferably a chlorine ion or ethyl sulfate ion.

The polymer compound (A) has monomer units (a1) and (a2) represented respectively by the formulae (2) and (3) wherein (a1) and (a2) are contained in a (a1)/(a2) molar ratio of 1/1500 to 30/100, preferably 1/1200 to 10/100, more preferably 1/1000 to 5/100.

The polymer compound (A) can be obtained according to a known method such as radical polymerization by copolymerizing monomer (a1') and monomer (a2') from which the vinyl monomer units (a1) and (a2) are derived. The vinyl monomer unit (a1) can al so be introduced by reacting Z—(OR$^{2c}$)$_q$-E-R$^{2f}$ with a polymer compound obtained by copolymerizing a polymerizable monomer (a1'') represented by C(R$^{2a}$)(R$^{2b}$)=C(R$^{2c}$)(Y') with a monomer from which the monomer unit (a2) is derived. Y' and Z are a reaction group which reacts to form B—R$^{2d}$—(OR$^{2e}$)$_q$-E-R$^{2f}$.

Specific examples of the vinyl monomer unit (a1') from which (a1) is derived can include the following compounds:

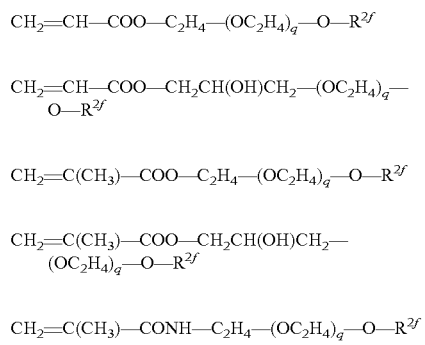

Specific examples of the vinyl monomer unit (a2') from which (a2) is derived can include the following compounds: (meth)acrylic acid, maleic acid, α-hydroxyacrylic acid, polyoxyalkylene wherein the average number of moles added is 2 to 50, preferably 2 to 40, more preferably 2 to 30, even more preferably 2 to 20, even more preferably 10 to 20 (preferably ethylene)mono(meth)acrylate, dialkyl(meth)acrylate (C1 to C3) amide, (meth)acrylic acid mono(di)alkanol (C2 to C3) amide, vinyl acetate which can be converted into a vinyl alcohol structure by saponification after polymerization, N-(meth)acryloyloxyalkyl (C1 to C3)-N,N-dialkyl (C1 to C3) amine, N-(meth)acryloyloxyalkyl (C1 to C3)-N,N,N-dialkyl (C1 to C3) ammonium salt, N-(meth)acryloylaminoalkyl (C1 to C3)-N,N-dialkyl (C1 to C3) amine, N-(meth)acryloylaminoalkyl (C1 to C3)-N,N-dialkanol (C1 to C3) amine, N-(meth)acryloylaminoalkyl (C1 to C3)-N,N,N-dialkyl (C1 to C3) ammonium salt, N-vinylpyrrolidone, N-vinylimidazole, and N-vinyl-2-caprolactam.

The monomer unit (a1) can also be obtained by copolymerizing the monomer selected from (a2') with vinyl acetate, then saponifying the resulting copolymer, and reacting a glycidyl ether compound represented by:

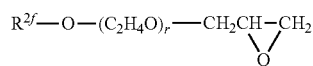

with OH of a vinyl alcohol unit of the resulting saponified product. Alternatively, the monomer unit (a1) can be obtained by copolymerizing the monomer selected from (a2') with a polyoxyethylene vinyl ether wherein the average number of moles added is 1 to 200, preferably 1 to 100, more preferably 1 to 50, and then reacting the product with a compound represented by:

Alternatively, the monomer unit (a1) can be obtained by copolymerizing the monomer selected from (a2') with vinyl acetate and then saponifying the resulting copolymer, followed by esterification reaction (or ester exchange reaction) between OH of a vinyl alcohol unit of the resulting saponified product and polyoxyethylene alkyl ether carboxylic acid represented by $R^{2f}$—O—$(C_2H_4O)_q$—$CH_2COX'$ wherein X' is —OH, —Cl, —$OCH_3$ or —$OC_2H_4$. Alternatively, the monomer unit (a1) can be obtained by copolymerizing the monomer selected from (a2') with a polyoxyethylene vinyl ether wherein the average number of moles added is 1 to 200, preferably 1 to 100, more preferably 1 to 50 and subsequent esterification reaction (or ester exchange reaction) of the resulting copolymer with a carboxylic acid represented by $R^{2f}$—COX.

The polymer compound (A) is a polymer compound having the vinyl monomers (a1) and (a2) in an amount of 50 to 100 mol %, preferably 60 to 100 mol %, more preferably 70 to 100 mol %, in the molecule, and can also be copolymerized with other monomers capable of copolymerizing with the vinyl monomer (a1') or (a1") and (a2'). The copolymerizable monomers can include compounds such as ethylene, propylene, N-butylene, isobutylene, N-pentene, 2-methyl-1-butene, N-hexene, 2-methyl-1-pentene, 2-ethyl-1-butene, styrene and vinyl toluene.

The polymer compound (A) is produced particularly preferably by a radical polymerization method, and the radical polymerization method can be carried out in a bulk, solution or emulsion system. The radical polymerization may be initiated by heating, and the initiator includes azo-type initiators such as 2,2'-azobis(2-amidinopropane)dihydrochloride, 2,2'-azobis(N,N-dimethyleneisobutylamidine)dihydrochloride etc., hydrogen peroxide, organic peroxides such as benzoyl peroxide, t-butyl hydroperoxide etc., persulfates such as sodium persulfate etc. Alternatively, the polymerization can be initiated by radical initiators other than those mentioned above, for example by redox initiators such as hydrogen peroxide-$Fe^{3+}$ or by irradiation with lights or radiations in the presence and/or absence of a photosensitizer.

The number-average molecular weight of the polymer compound (A) in the present invention is preferably 2,000 to 200,000, more preferably 3,000 to 150,000, even more preferably 4,000 to 120,000. The weight-average molecular weight can be determined by gel permeation chromatography with polyethylene glycol as standard.

<Polymer Compound (B)>

The polymer compound (B) preferable as the component (a) in the present invention is a polyglyceryl ether compound whose OH groups are partially groups represented by J-$R^{6a}$—$(OR^{6b})_r$-L-$R^{6c}$. By addition reaction of glycidyl ether, the polyglyceryl ether can be produced as a random addition product having a unit represented by the formula (4) having glycidyl ether added to OH at the position 1 or 3 of the glycerol group and a unit represented by the formula (5) having glycidyl ether added to OH at the position 2 of the glycerol group. The proportion of the units of the formulae (4) and (5) can be arbitrarily selected without influencing the effect of the present invention.

The polymer compound (B) can be produced by reaction of a part of hydroxy groups of the polyglyceryl ether compound containing the units of the formulae (4) and (5) with W—$(OR^{6b})_r$-L-$R^{6c}$. In this formula, W is a group reacting with OH of the polyglyceryl ether to form -J-$R^{6a}$—$(OR^{6b})_r$-L-$R^{6c}$. Specific examples of W—$(OR^{6b})_r$-L-$R^{6c}$ can include the following compounds:

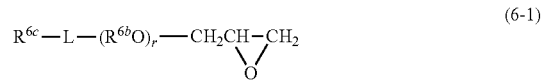 (6-1)

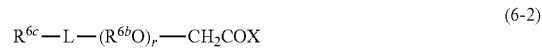 (6-2)

wherein X is —OH, —Cl, —OCH, or —$OC_2H_4$.

These compounds can be reacted with OH of the polyglyceryl ether by using a usually known method, and for example, the compound of the formula (6-1) can be easily reacted by using an alkali such as NaOH or KOH as a catalyst. When the compound of the formula (6-2) is used, well-known esterification reaction or ester exchange reaction can be used.

The polymer compound (B) in the present invention can contain unit (a5) other than the units (a3) and (a4), and specific examples of (a5) can include:

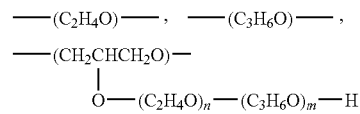

wherein n is a number of 0 to 50, m is a number of 0 to 20, and n+m is a number of 1 to 50.

The molar ratio of (a4)/(a3) in the polymer compound (B) is 1/1500 to 30/100, preferably 1/1200 to 10/100, more preferably 1/1000 to 5/100, and the proportion of (a3) and (a4) in total in the molecule is 50 to 100 mol %, preferably 60 to 100 mol %, more preferably 70 to 100 mol %. The number-average molecular weight of the polymer compound (B) is preferably 500 to 20,000, more preferably 1,000 to 10,000, even more preferably 3,000 to 8,000. The weight-average molecular weight can be determined by gel permeation chromatography with polyethylene glycol as standard.

The component (a) in the present invention, though being a water-soluble polymer compound, partially has a hydrophobic group as $R^{1c}$. On one hand, allergen particularly mite allergen is water-soluble. By using the component (a) in the present invention as an aqueous composition dissolved in water, allergen contacted with, and dissolved in, the aqueous composition is estimated to have a structure wherein the allergen is included in hydrophobic groups of the component (a) in solution. As a result, the allergen comes to be in a state covered with the polymer compound thus hardly exhibiting its allergic action; this can be regarded as reduction in the allergen.

The allergen-reducing agent of the present invention preferably contains the component (a) in an amount of 0.005 to 10 wt %, more preferably 0.01 to 5 wt %, even more preferably 0.05 to 1 wt %.

Unless the effect of the present invention is hindered, the allergen-reducing agent of the present invention can contain a polymer compound other than the component (a) and can particularly use a water-soluble polymer compound having units having hydroxy or carboxy groups wherein at least a part of hydrogen atoms of the hydroxy or carboxy groups are substituted by groups represented by the formula (1) above.

The allergen-reducing agent of the present invention not only contains arbitrary ingredients described below, but also water [hereinafter, referred to as component (b)] that is the balance. The water is preferably as pure as possible, but may be in such a grade as to be substantially free from contaminant compounds which can act as allergens. Specifically, sterilized water sterilized with chlorine etc., or ion exchange water or the like from which metal components such as calcium present in a trace amount were removed, can be used.

The component (b) is incorporated as the balance to serve as a solvent for component (a) etc., and for spraying into space, is incorporated preferably in an amount of 60 wt % or more (excluding a propellant), or for direct spraying onto a solid surface, is incorporated preferably in an amount of 80 wt % or more, more preferably 90 wt % or more, and the upper limit is preferably 99.995 wt % or less.

For the purpose of increasing the drying of liquid droplets sprayed into space, increasing the drying of the composition contacted with the surface of an object and improving the stability of the component (a) in the allergen-reducing agent of the present invention, the allergen-reducing agent preferably contain a water-soluble organic solvent (hereinafter, referred to as component (c)), more preferably a water-soluble organic solvent forming an azeotropic mixture with water and having an azeotropic point of lower than 100° C. with water at 1013.25 hPa (760 mmHg), and among compounds forming azeotropic mixtures with water described in Table 8-43 on page II-147 in "Kagaku Binran Kisohen" (Handbook of Chemistry, Fundamental Version), 4th edition, edited by the Chemical Society of Japan and published by Maruzen Co., Ltd., compounds having an azeotropic point of lower than 100° C., preferably 60 to 90° C., are preferably used. Preferable examples of the component (c) include ethanol, cyclohexane, 2-butanol, cyclohexanol, cyclohexanone, cyclohexane, toluene, 1-butanol, 2-butanol, 1-propanol, 2-propanol, 1-hexanol, hexane, 1-heptanol, 1-pentanol, 2-pentanol etc., and C2 to C7 alcohol compounds are preferable. In particular, ethanol, 1-propanol and 2-propanol are even more preferable in respect of the effect of removing allergen.

The content of the component (c) in the allergen-reducing agent of the present invention is preferably 0 to 50 wt %, more preferably 0.5 to 20 wt %, even more preferably 1 to 18 wt %. When the allergen-reducing agent of the present invention is used in a method of removing allergen which includes applying or spraying the allergen-reducing agent onto the rigid surface of flooring or the like and then wiping it off with an absorbent or in a method of using a flexible sheet (e.g. a nonwoven fabric) impregnated with the allergen-reducing agent of the present invention, the incorporation of the component (c) in an amount of preferably 8 wt % or less, more preferably 5 wt % or less, into the allergen-reducing agent of the present invention is more preferable than increasing the drying speed, in order to make allergen sufficiently harmless by preferentially dissolving the allergen in, and sufficiently incorporating it into, the aqueous solution. When the allergen-reducing agent is used in spraying for a method of removing allergen in space, the component (c) is incorporated in an amount of preferably 5 wt % or more, more preferably 8 to 20 wt %, into the allergen-reducing agent of the present invention.

In the present invention, a repellent against arthropods (hereinafter, referred to as component (d)) is preferably contained, and the allergen-reducing agent of the present invention containing the component (d) can be continuously used to repel arthropods such as mites, to reduce the absolute amount of allergic substances derived from arthropods. The arthropod repellent in the present invention is defined as a substance having a repellent effect on *Dermatophagoides farinae*, and is a substance by which the degree of repellency of *Dermatophagoides farinae* becomes 50% or more in the following entry inhibition method.

Method of Measuring the Degree of Repellency (Entry Inhibition Method)

Test medium: A 9-cm Petri dish is fixed to an adhesive sheet plate, and about 10,000 mites (*Dermatophagoides farinae*) together with a medium are placed in the dish. In the center of the Petri dish, a Petri dish of 4 cm in diameter is then placed, and a paper filter cut in the same diameter is placed in the bottom and impregnated with 0.5 ml of 10 wt % test substance in ethanol. 500 mg feed having a mouse powder feed mixed with dry yeast is placed in the center of the filter paper. Comparative medium: A comparative medium is prepared in the same manner as above except that another 9-cm Petri dish is fixed to the same adhesive sheet plate, and in the test medium, ethanol alone is used as the solution with which the filter paper is impregnated.

These Petri dishes are placed under the condition of 25° C./75% RH, and 48 hours later, mites having entered the feed in the center are counted, and from a difference in count between the test medium and comparative medium, the degree of repellency (%) is calculated according to the following equation. The mites are counted under a stereoscopic microscope.

$$\text{Degree of repellency (\%)}=(1-\text{number of entering mites in the test medium}/\text{number of entering mites in the comparative medium})\times 100$$

A compound preferable in respect of safety as the component (d) in the present invention is an extract obtained from a natural material, a compound obtained by isolating, from a natural material, a compound occurring in an extract of the natural material, or a compound obtained by synthesizing a compound occurring in an extract of a natural material, and a mixture thereof, and specifically the following compounds are preferable.

(d-1): a single synthetic or isolated perfume, or a mixture of two or more perfumes, selected from tetrahydrolinalool, bornyl acetate, myrcenyl acetate, cedryl acetate, lavandulyl acetate, citronellyl isobutyrate, terpinyl propionate, linalyl formate, citronellyl tigrate, nopyl acetate, vetiveryl acetate, lyral, citronellyloxyacetaldehyde, 2,6,10-trimethyl-9-undecanal, α-ionone, β-ionone, irone, α-damascone, β-damascone, nootkatone, cedryl methyl ether, isomenthone, citronellal, linalool, cintronellol, citral, L-menthol, p-menthane, α-pinene, β-pinene, d-limonene, geraniol, α-terpineol, β-terpineol, γ-terpineol, 1,8-cineol, p-menthan-8-ene-1,2-diol, eugenol, benzyl formate, benzyl acetate, benzyl propionate, benzyl butyrate, benzyl valerate, benzyl caproate, benzyl phenyl ketone, benzophenone, linalool, α-hexyl succinic aldehyde, coniferyl aldehyde, jasmone, dihydrojasmone, methyl jasmonate and methyl dihydrojasmonate;

(d-2): a single vegetable essential oil, or a mixture of two or more vegetable essential oils, selected from lemon grass oil, lavender oil, orange oil, vetiver oil, patchouli oil, cananga oil, clove oil, cajeput oil, citronella oil, natsumegu oil, pepper oil, sandal wood oil, bulk oil, cagin oil, ginger oil, campo oil, cubeba oil, lemon grass oil, cone mint oil, anise oil, lang oil, cinnamon oil, mease oil, palomarosa oil, fennel oil, calamus oil, taimes oil, neam oil, cinnamon leaf oil and cedar wood oil;

(d-3): hinokitiol and/or hinokitiol derivatives; and (d-4): a plant extract extracted with alcohol from persimmon leaves, Japanese fatsia, mugwort, celery and hottuynia cordata.

In the present invention, the compounds (d-1) and (d-2) are particularly preferable, and the compound (d-1) is particularly preferably jasmone, dihydrojasmone, methyl jasmonate or methyl dihydrojasmonate, and the vegetable essential oil (d-2) is particularly preferably calamus oil, cinnamon leaf oil, clove oil, lemon grass oil or cedar wood oil.

The allergen-reducing agent according to the present invention contains the component (d) preferably in an amount of 0.001 to 2 wt %, more preferably 0.005 to 1 wt %, even more preferably 0.01 to 0.5 wt %. A perfume component when incorporated in addition to the component (d) is incorporated such that the total amount of the perfume component and the component (d) is preferably 2 wt % or less, more preferably 1 wt % or less, even more preferably 0.5 wt % or less.

In the present invention, a sterilizing agent (hereinafter, referred to as component (e)) is preferably contained, and it adheres to mold spores etc. known as allergic substances floating in air to prevent propagation of molds etc. and reduce the absolute amount of allergenic substances derived from the molds.

The antibacterial compound as the component (e) in the present invention is a compound indicating an inhibition band in an antibacterial test carried out according to a method JIS L 1902 "Antibacterial Test Method of Fibrous Products" using a cloth having 1 wt % of the compound adhering uniformly to cotton calico #2003. The compound can be selected from compounds described on pp. 501-564 in "Kosyohin, Iyakuhinbofu Sakkinzai No Kagaku" (Science of Perfumes, Cosmetics, Pharmaceutical Preservatives and Bactericidal Agents) (authored by Koichi Yoshimura & Hirofumi Takigawa and published on Apr. 10, 1990 by Flagrance Journal Ltd.).

The component (e) in the present invention is particularly preferably one of the following antibacterial compounds (I) to (IV):

(I) a quaternary ammonium group-free antibacterial compound (excluding an organic peracid or organic peroxide) having a solubility of 1 g/100 g or lower, preferably 0.5 g/100 g or lower, in water at 20° C., a molecular weight of 100 to 420, preferably 150 to 410, and a melting point of 40° C. or more;

(II) a water-soluble quaternary ammonium antibacterial compound having a solubility of 2 g/100 g or higher, preferably 5 g/100 g or higher, in water at 0° C. and having at least one C8 to C16 alkyl group;

(III) at least one antibacterial compound selected from 2-(4-thiocyanomethylthio)benzimidazole, polylysine, polyhexamethylene biguanide and glucuronic acid chlorohexizine; and (IV) a salt of a metal selected from silver, copper and zinc, having a solubility of higher than 1 g/100 g in water at 20° C.

The compound satisfying the properties (I) is preferably at least one member selected from triclosan, bis-(2-pyridiothio-1-oxide) zinc, 2,4,5,6-tetrachloroisophthalonitrile, trichlorocarbanilide, 8-oxyquinoline, dehydroacetic acid, benzoic esters, chlorocresols, chlorothymol, chlorophene, dichlorophene, bromochlorophene and hexachlorophene. Particularly, triclosan is preferable because it has an excellent effect for the object of the present invention. Triclosan derivatives described in JP-A 11-189975 are also favorable, and specifically dichlorohydroxy diphenyl ether or monochlorohydroxy diphenyl ether is preferable.

As the compound (II), it is also preferable to use a quaternary ammonium compound represented by the following formula (8) or (9):

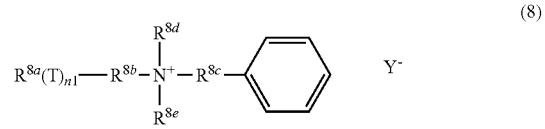

wherein $R^{8a}$ and $R^{9a}$ each represent a C5 to C16, preferably C7 to C16, alkyl group or alkenyl group, preferably alkyl group, $R^{8d}$ and $R^{8e}$ each represent a C1 to C3 alkyl group or hydroxyalkyl group, and T is —COO—, —COO—, —CONH—, —NHCO— or

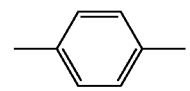

n1 is 0 or 1. $R^{8b}$ or $R^{8c}$ is a C1 to C6 alkylene group or —(O—$R^{8f}$)$_{m1}$— wherein $R^{8f}$ is an ethylene group or propylene group, preferably an ethylene group, m1 is a number of 1 to 10, preferably 1 to 5, and Y⁻ is an anion group, preferably a halogen ion, or a C1 to C3 alkyl sulfate ion.

An even more preferable quaternary ammonium compound includes the following compounds. Y⁻ in the formula has the same meaning as defined above.

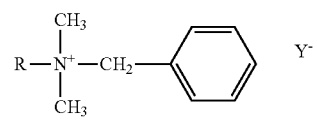

wherein R is a C8 to C16 alkyl group.

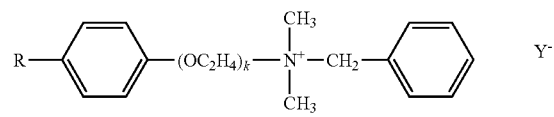

wherein R is an optionally branched C6 to C10 alkyl group, and k is a number of 1 to 5.

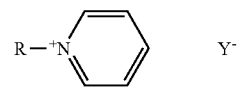

wherein R is a C8 to C18 alkyl group.

The compound (III) is particularly preferably polylysine.

As the compound (IV), a compound having a solubility of higher than 1 g/100 g in water at 20° C. can be selected from compounds containing silver, copper and zinc described on pages II-166 to II-177 and in Table 8-42 in "Kagaku Binran Kisohen" (Handbook of Chemistry, Fundamental Version), 3rd edition. Among these compounds, zinc salts are preferable in the present invention, and particularly a compound selected from zinc sulfate, zinc chloride and zinc acetate is preferable.

The component (e) in the present invention is even more preferably at least one member selected from triclosan, the compound of the formula (8), polylysine, zinc sulfate, zinc chloride and zinc acetate, in order to achieve a preferable effect on reduction of allergen.

The content of the component (e) in the allergen-reducing agent of the present invention is preferably 5 wt % or less, more preferably 0.001 to 3 wt %, even more preferably 0.005 to 2 wt %.

The allergen-reducing agent of the present invention is in the form of an aqueous solution (dispersed component may be present) having the component (a) and, if desired, the components (c) to (e) dissolved in water of the component (b). The pH value of the allergen-reducing agent of the present invention at 20° C. is preferably 5.5 to 8.5, more preferably 6.5 to 8.0, from the viewpoint of safety and damage to a base material. As a pH adjusting agent, acids, for example inorganic acids such as hydrochloric acid and sulfuric acid, organic acids such as citric acid, succinic acid, malic acid, fumaric acid, tartaric acid, malonic acid and maleic acid, and alkalis, for example alkali metal hydroxides such as sodium hydroxide and potassium hydroxide, carbonates such as sodium carbonate and potassium carbonate, ammonia and derivatives thereof, and amine compounds such as monoethanol amine, diethanol amine, triethanol amine, aminomethyl propanol and aminomethyl ethanol are preferably used alone or as a mixture thereof. In the present invention, a substance other than the component (a), which solidifies upon drying, is in a solid state at 30° C. or less and does not exhibit adhesiveness or film-forming properties, exhibits solidifying properties with allergens aggregated at the time of drying, and is thus preferably used, for the purpose of improving physical allergen removability. From the viewpoint of making allergen harmless, the allergen reducing effect can be achieved even if the amount of such solidifying substance is less than 0.01 wt %. For allergen on a rigid surface or in space, the amount of the solidifying substance is preferably smaller, and the amount of the solidifying substance in the allergen-reducing agent is designed to be incorporated preferably in an amount of 1 wt % or less, more preferably 0.1 wt % or less, even more preferably 0.05 wt % or less, and accordingly the concentration of the pH adjusting agent is also regulated in consideration of this aspect. The loss by drying (described in JIS K0067, a method of drying under heating at atmospheric pressure, 105° C./2 hours) in the allergen-reducing agent of the present invention is preferably 95% or more, more preferably 98% or more, even more preferably 99% or more, even more preferably 99.5% or more.

The allergen-reducing agent of the present invention can be blended not only with the components (a) to (e) but also with a surfactant such as alkyl glucoside other than the component (e), a chelating agent such as citric acid, a water-soluble solvent for example glycol such as diethylene glycol monobutyl ether etc., a thickener such as xanthane gum etc., an anti-fungus agent/antiseptic, and a perfume other than the component (c), and in use of these components, there is need for consideration of the safety and physical properties of the allergen-reducing agent as well as for sufficient consideration of allergy. The total amount of the components other than the components (a) to (e) is preferably 2 wt % or less, more preferably 1.5 wt % or less, even more preferably 1 wt % or less.

One application form of the allergen-reducing agent of the present invention includes the allergen-reducing agent contained in a spray container, which contains the allergen-reducing agent with which a container equipped with a spray device is charged. Another application form includes an allergen-reducing sheet containing a flexible sheet impregnated with the allergen-reducing agent of the present invention. This allergen-reducing sheet can be used in a cleaning method which includes wiping the surface of an object with the sheet and subsequent cleaning by vacuuming or sweeping cleaning. In connection with this, there is provided the allergen-reducing agent of the present invention provided with an indication to the effect that it is used in such specific cleaning method, as well as the allergen-reducing sheet of the present invention provided with the same indication.

The allergen-reducing agent contained in a spray container is used in a method of making allergen harmless by spraying it into allergen-floating space and in a method of making allergen harmless on the surface of a treatment object by directly spraying it onto the object.

By spraying the allergen-reducing agent from the spray container, it is contacted with floating allergen or an allergen precursor. A majority of allergen substances are water-soluble compounds, and these compounds are dissolved in liquid droplets of the allergen-reducing agent and contacted with the component (a). In the present invention, the component (a) has an effect of inactivating allergen itself in addition to the effect of aggregation/sedimentation described above, and even after sedimentation, the contact of allergen with the human body can be prevented to remove allergen and its precursor effectively. In connection with this method, the allergen-reducing agent of the present invention provided with an indication to the effect that it is used in the allergen reducing method of spraying into space can be provided according to the present invention.

The method of directly spraying the allergen-reducing agent of the present invention onto a treatment object is effective particularly for the rigid surface of a floor or the like, and In this case, the allergen-reducing agent after spraying is wiped off with a water-absorbing article, for example an absorbent such as a liquid-absorbing cloth, before the allergen-reducing agent is not dried, whereby allergen can be removed by absorption into the absorbent. Generally, when one absorbent is repeatedly used in wiping treatment, there is the case where allergen removed once by absorption into the absorbent adheres again to a rigid surface, so a sufficient allergen reducing effect may not be obtained. In the present invention, however, there is no such problem. This is because even if allergen adheres again to a treatment surface, the allergen dissolved once in the allergen-reducing agent of the present invention has been made harmless by the component (a). Accordingly, the method described above may use an absorbent impregnated with the allergen-reducing agent. The allergen-reducing agent of the present invention is sprayed directly onto the surface of an object and then dried, which may be followed by cleaning with a cleaner. In this case, the allergen made harmless by the component (a) in the present invention is hardly stirred up and can thus be easily removed by a cleaner. Generally, allergen is a very light substance and easily scatters even by movement of human, but when the allergen-reducing agent of the present invention is used, there can be obtained an excellent effect of making allergen harmless and simultaneously preventing scattering.

A spraying method using a propellant such as aerosol as a spray device is also feasible, but in the present invention, a trigger sprayer is preferably used. The trigger sprayer is preferably the one jetting the agent in an amount of 0.1 to 2.0 g, preferably 0.2 to 1.5 g, more preferably 0.3 to 1.0 g, by one stroke. As the container in the trigger sprayer used in the present invention, a pressure-accumulating trigger disclosed in Japanese Utility Model Application Laid-Open (JP-U) No. 4-37554 is particularly excellent in respect of spraying uniformity.

With respect to jetting properties, the trigger sprayer is preferably a pressure-accumulating trigger sprayer which sprays a liquid on an area of 100 to 800 $cm^2$, preferably 150 to 600 $cm^2$, when an object placed vertically on the ground is sprayed with the liquid from a place apart by 15 cm. In the present invention, the component (a) is sprayed preferably in an amount of 10 to 4000 mg, more preferably 50 to 4000 mg, per $m^3$ of space, in order to bring about a higher effect of removing allergen.

The sprayer used for spraying into space is a sprayer not foaming the liquid upon spraying, in order to make liquid droplets smaller. It follows that preferably the incorporation of a surfactant exhibiting foaming properties is substantially avoided.

On the other hand, a flexible sheet for impregnation, used in an allergen-reducing sheet impregnated with the allergen-reducing agent, is preferably a cellulose fiber-containing fiber structure or a laminate of fiber structures. The fiber structure includes a nonwoven fabric, a woven fabric and a knit cloth, and in the present invention, a nonwoven fabric is particularly preferably used in respect of cleaning properties. The cellulose fiber includes naturally occurring fibers such as cotton and hemp, cellulose-based chemical fibers such as viscous rayon, TENCEL and acetate, and in the present invention, rayon is used even more preferably because of an excellent effect of removing allergen etc. Usable fibers other than cellulose fibers include polyolefin fibers such as polyethylene (PE) and polypropylene (PP), polyester fibers such as polyethylene terephthalate, polyamide fibers such as nylon, polyacrylonitrile fibers and polyvinyl alcohol fibers. The thickness of the flexible sheet in a dry state is preferably 0.2 to 10 mm, more preferably 0.4 to 5 mm, under a load of 3 $g/m^2$. The flexible sheet preferably has water retention properties by which water that is 1 to 4 times as high as the weight of the sheet can be retained. With respect to the degree of impregnation, the flexible sheet is impregnated with the allergen-reducing agent in a weight ratio of preferably 1.5 to 5, more preferably 2.2 to 3.5, particularly to the fiber structure. The amount of the allergen-reducing agent contained in the sheet varies depending on the fiber diameter and basis weight of the fiber structure.

In the present invention, the fiber structure serving as the flexible sheet contains cellulose fibers in an amount of preferably 40 to 100 wt %, more preferably 50 to 90 wt %, in the fiber structure.

The density (bulk density) of the fiber structure serving as the flexible sheet is preferably 0.01 to 1.0 $g/cm^3$, more preferably 0.05 to 0.5 $g/cm^3$, even more preferably 0.1 to 0.3 $g/cm^3$, under a load of 3.0 $gf/cm^2$. The basis weight is preferably 5 to 150 $g/m^2$, more preferably 10 to 100 $g/m^2$, even more preferably 20 to 70 $g/m^2$.

When a nonwoven fabric is used in the flexible sheet in the present invention, mention is made of spun lace, spun bond, melt blown, needle punch and/or stitch bond in addition to wet nonwoven fabrics and dry nonwoven fabrics such as chemical bond, thermal bond (air-through) and air-laid, and particularly one or more members selected from wet nonwoven fabrics, chemical bond, thermal bond (air-through), melt blown and spun lace are effective in respect of the effect of the invention. Low-interweaved nonwoven fabrics composed of fibers having a fiber length of 20 mm or more, particularly 30 to 100 mm, especially 35 to 65 mm, are preferably used.

Such low-interweaved nonwoven fabrics include spun lace nonwoven fabrics, thermal bond nonwoven fabrics such as air-through, spun bond nonwoven fabrics, and three-dimensionally raised nonwoven fabrics. In this case, a low-interweaved nonwoven fabric composed of fibers having a fiber length of 20 mm or more does not require the fiber lengths of all constituent fibers to be 20 mm or more, and incorporation of fibers with a fiber length of less than 20 mm inevitably mixed and/or generated in a starting material of the nonwoven fabric and/or in the production process is allowed. Formation of a large number of embossed portions on the surface of the wiping material of the present invention by thermal embossing is preferable in respect of improvement in operativeness at the time of cleaning (reduction in frictional resistance).

The present invention also provides the following cleaning method for reducing allergen. That is, the cleaning method includes spraying or applying the allergen-reducing agent of the present invention onto the surface of an object before cleaning by vacuuming or sweeping cleaning and then wiping it off with a water-absorbing article before the allergen-reducing agent is dried. Cleaning by vacuuming or sweeping cleaning causes allergen to be scattered, and thus a more sufficient effect can be obtained by previous allergen reducing treatment than by allergen reducing treatment after cleaning. The cleaning method of the present invention unlike conventional wiping cleaning involves treating a rigid surface with the allergen-reducing agent of the present invention prior to the cleaning, whereby excellent removability of allergen can be achieved. For the water-absorbing article used in wiping, the description of the flexible sheet can be referred to. The method of the present invention also involves wiping a water-absorbing article impregnated with the allergen-reducing agent of the present invention. In connection with this, the present invention provides the allergen-reducing agent of the present invention provided with an indication to the effect that it is used in such specific cleaning method.

The allergen-reducing agent contained in a spray container is used in a method of directly spraying it onto a treatment object to make allergen harmless on the surface of the object. As used herein, the surface of the object refers to any surface to which allergen can adhere, and includes the floor surface of flooring, a cushion floor, a tatami mat etc. and the surface of furniture made of wood, leather, glass, metal and plastics and the surface of electrical appliances and coated surfaces thereof.

As the water-absorbing article, it is possible to use a liquid-absorbing article, for example a cloth such as a dustcloth etc., a nonwoven fabric, and a porous article such as sponge and paper. Particularly, a nonwoven fabric and sponge are preferable in respect of operativeness and the amount of retainable liquid, and the form is preferably a sheet shape or roller shape. Generally, when one absorbent is used repeatedly in wiping treatment, there is the case where allergen removed once by absorption into the absorbent adheres again to a rigid surface, and thus a sufficient allergen reducing effect may not be obtained. In the present invention, however, there is no such problem. This is because even if allergen adheres again to a treatment surface, the allergen dissolved once in the allergen-reducing agent of the present invention has been made harmless by the component (a). Accordingly, the method described above may use an absorbent impregnated with the allergen-reducing agent. As a matter of course, a means for preventing re-adhesion is preferably taken, and in this case, an absorbent containing cellulose fibers is preferably used, and specifically a fiber structure containing cellulose fibers described later can be used.

As described above, the allergen-reducing agent of the present invention is used in the allergen reducing method which includes spraying or applying it onto the surface of an object and then wiping it off with a water-absorbing article before the allergen-reducing agent is dried, and thus the present invention also provides the allergen-reducing agent of the present invention provided with an indication to the effect that it is used in the specific allergen reducing method.

The present invention provides a cleaning method wherein before cleaning by vacuuming or sweeping cleaning, the allergen-reducing agent of the present invention is sprayed or applied onto the surface of an object and wiped off with a water-absorbing article before drying (hereinafter, referred to as cleaning method 1). The present invention also provides a cleaning method wherein the surface of an object is wiped with the above-described allergen-reducing sheet having a flexible sheet impregnated with the allergen-reducing agent of the present invention and then cleaned by vacuuming or by sweeping (hereinafter, referred to as cleaning method 2). Cleaning by vacuuming or sweeping cleaning causes allergen to be scattered, so a more sufficient effect can be obtained by previous allergen reducing treatment than by allergen reducing treatment after cleaning. Particularly, the cleaning method 1 of the present invention unlike conventional wiping cleaning involves treating a rigid surface with the allergen-reducing agent of the present invention prior to the cleaning, whereby excellent removability of allergen can be achieved. For the water-absorbing article used in wiping, the description of the flexible sheet can be referred to. The present invention also includes a method of wiping with a water-absorbing article impregnated with the allergen-reducing agent of the present invention. In connection with this, the present invention provides the allergen-reducing agent of the present invention provided with an indication to the effect that it is used in the specific cleaning method 1 or 2.

When the allergen-reducing agent of the present invention is applied onto the surface of an object, a cloth such as a dustcloth, a nonwoven fabric, a porous article such as sponge or paper, or an article such as a brush capable of retaining liquid can be used, or the allergen-reducing agent can be applied by hand or with a device such as a spatula, scraper or roller. Particularly, a nonwoven fabric and sponge are preferable in respect of operativeness and the amount of retainable liquid, and the form is preferably a sheet shape or roller shape.

When $R^{1c}$ is a hydrocarbon group having a steroid skeleton, the following compounds can also be used in the allergen-reducing agent and method of the present invention.

That is, the present invention provides a cholesteryl polysaccharide derivative wherein a part or all of hydrogen atoms of hydroxy groups in a polysaccharide or its derivative are substituted by the following group (A):
(A) Group represented by the following formula (1p) [hydrogen atom of a hydroxy group of the substituent group (A) may be further substituted by the substituent group (A)]

$$-E^1-(OA)n-E^2-R \qquad (1p)$$

wherein $E^1$ represents a C1 to C6 linear or branched divalent saturated hydrocarbon group whose hydroxy group or oxo group may be substituted, n is a number of 5 to 30, A's whose number is n are the same or different and each represent a C1 to C6 linear or branched divalent saturated hydrocarbon group, $E^2$ represents an ether linkage or an oxycarbonyl group (—OCO— or —COO—) and R represents a hydrocarbon group having a steroid skeleton, as well as a process for producing the same.

Further, the present invention provides a process for producing the polysaccharide derivative of the present invention, which includes reacting a polysaccharide or its derivative with a polyoxyalkylenating agent represented by (a) the following formula (3p):

$$E^3-(OA)_n-E^2-R \qquad (3p)$$

wherein $E^3$ is a C3 to C6 epoxylated alkyl group, a C1 to C6 linear or branched halogenated alkyl group whose hydroxy group may be substituted, a carboxy group, or a C2 to C6 carboxyalkyl group or a derivative thereof, n is a number of 5 or 30, A's whose number is n are the same or different and each represent a C1 to C6 linear or branched divalent saturated hydrocarbon group, $E^2$ represents an ether linkage or oxycarbonyl group (—OCO— or —COO—) and R represents a hydrocarbon group having a steroid skeleton.

When cellulose is used as the polysaccharide or its derivative, the repeating unit of the polysaccharide derivative of the present invention is represented by the following formula:

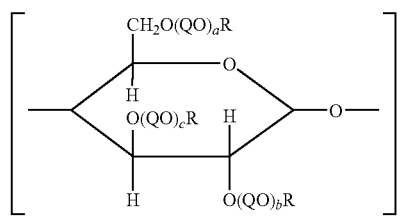

wherein R's are the same or different and each represent a group selected from (1) a hydrogen atom, methyl group, ethyl group, hydroxyethyl group and hydroxypropyl group, (2) a substituent group (A) containing a polyoxyalkylene group, (3) a sulfoalkyl group (B), (4) a carboxyalkyl group (C), and (5) a cationic substituent group (D), Q's are the same or different and each represent a C2 to C4 alkylene group, and a, b and c are the same or different and each represent a number of 0 to 10. The QO group, R group, a, b and c in the repeating unit or among the repeating units may be the same or different, and hydroxy groups of the substituent groups (A) to (D) may be further substituted with other substituent groups (A) to (D), provided that the repeating unit has at least the substituent group (A) as R.

$E^1$ in the formula (1p) for the substituent group (A) containing a polyoxyalkylene group is preferably a C2 or C3 group, and preferable examples include ethylene, propylene, trimethylene, 2-hydroxytrimethylene, 1-hydroxymethylethylene, 1-oxoethylene, 1-oxotrimethylene, 1-methyl-2-oxoethylene etc.

A in the formula (1p) is preferably a C2 or C3 group, and preferable examples include ethylene, propylene and trimethylene. The polymerization degree of (—OA—), represented by n, is preferably 5 to 30, more preferably 5 to 25, in respect of the thickening effect and emulsion stability, and A's whose number is n may be the same or different. n is meant to be the average number of moles added. $E^2$ is an ether linkage or an oxycarbonyl group, preferably an ether linkage.

R in the formula (1p) is a hydrocarbon group having a steroid skeleton, particularly preferably a cholesteryl group.

The degree of substitution with the substituent group (A) in the polysaccharide derivative of the present invention is preferably in the range of 0.0001 to 1.0, more preferably 0.0005 to 0.5, even more preferably 0.001 to 0.1.

The polysaccharide derivative of the present invention may be substituted with one or more groups selected from the following substituent group (B), (C) and (D), in addition to the substituent group (A). Hydrogen atoms of hydroxy groups of the substituent groups (A) to (D) may further be substituted with one or more groups selected from the substituent groups (A) to (D).

(B) C1 to C5 sulfoalkyl group whose hydroxy group may be substituted, or a salt thereof.

The substituent group (B) includes a 2-sulfoethyl group, 3-sulfopropyl group, 3-sulfo-2-hydroxypropyl group, 2-sulfo-1-(hydroxymethyl)ethyl group etc., among which a 3-sulfo-2-hydroxypropyl group is preferable from the viewpoint of stability and producibility. All or a part of these substituent groups (B) may be salts with the group 1 or 2 elements such as Na, K, Ca and Mg or organic cations such as amines, ammonium etc. The degree of substitution with these substituent groups (B) is preferably in the range of 0 to 1.0, more preferably 0 to 0.8, even more preferably 0 to 0.5, per constituent monosaccharide residue.

(C) C2 to C6 carboxyalkyl group whose hydroxy group may be substituted, or a salt thereof.

The substituent group (C) includes a carboxymethyl group, carboxyethyl group, carboxypropyl group, carboxybutyl group and carboxypentyl group, among which a carboxymethyl group is preferable from the viewpoint of stability and productivity. All or a part of these substituent groups (C) may be salts with the group 1 or 2 elements such as Na, K, Ca and Mg or organic cations such as amine, ammonium etc. The degree of substitution with these substituent groups (C) is preferably in the range of 0 to 1.0, more preferably 0 to 0.8, even more preferably 0 to 0.5, per constituent monosaccharide residue.

(D) Group represented by the following formula (2p):

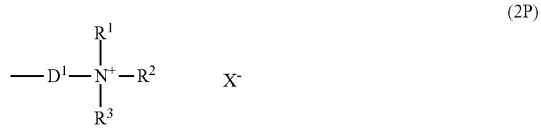

(2P)

wherein $D^1$ represents a C1 to C6 linear or branched divalent saturated hydrocarbon group whose hydroxy group may be substituted, $R^1$, $R^2$ and $R^3$ are the same or different and each represent a C1 to C3 linear or branched alkyl group whose hydroxy group may be substituted, and $X^-$ represents a hydroxy ion, halogen ion or organic acid ion.

D1 in the cationic substituent group (D) is preferably a C2 or C3 group, and preferable examples include ethylene, propylene, trimethylene, 2-hydroxytrimethylene, 1-hydroxymethylethylene etc.

$R^1$, $R^2$ and $R^3$ in the cationic substituent group (D) include a methyl group, ethyl group, propyl group, 2-hydroxyethyl group etc., among which a methyl group and ethyl group are preferable.

The halogen ion represented by $X^-$ in the cationic substituent group (D) includes a chlorine ion, bromine ion, iodine ion etc., and the organic acid ion represented by $X^-$ includes $CH_3COO^-$, $CH_3CH_2COO^-$, $CH_3(CH_2)_2COO^-$, etc. $X^-$ is preferably a hydroxy ion, chlorine ion or bromine ion.

The degree of substitution with these cationic substituent groups (D) is preferably in the range of 0 to 0.5, more preferably 0 to 0.3, per constituent monosaccharide residue.

The polysaccharide derivative of the present invention can be produced for example by reacting a polysaccharide or a derivative thereof with:

(a) a polyoxyalkylenating agent represented by the following formula (3p):

$$E^3\text{-}(OA)n\text{-}E^2\text{-}R \qquad (3p)$$

wherein $E^3$ represents a C3 to C6 epoxylated alkyl group, a C1 to C6 linear or branched halogenated alkyl group whose hydroxy group may be substituted, a carboxy group or a C2 to C6 carboxyalkyl group, or a derivative thereof, and n, A, $E^2$ and R each have the same meaning as defined above, or further reacting it with one or more compounds selected from the following (b), (c) and (d):

(b) a sulfonating agent selected from vinylsulfonic acid, a C1 to C5 haloalkanesulfonic acid whose hydroxy group may be substituted, C2 to C6 sulfonic acid having an epoxy group, and a salt thereof, (c) a carboxylating agent selected from C2 to C6 halogenated carboxylic acid whose hydroxy group may be substituted and a salt thereof, and (d) a cationizing agent represented by the following formula (4p):

(4P)

wherein $D^2$ is a C3 to 6 epoxylated alkyl group or a C1 to C6 linear or branched halogenated alkyl group which may have a hydroxy group and $R^1$, $R^2$, $R^3$ and $X^-$ each have the same meaning as defined above.

That is, the polysaccharide derivative of the present invention is obtained by polyoxyalkylenating all hydrogen atoms of hydroxy groups in a polysaccharide or a derivative thereof (introduction of substituent group (A)) or by polyoxyalkylenating a part of the hydrogen atoms (introduction of substituent group (A)), if necessary followed by sulfonation (introduction of sulfoalkyl group (B)), carboxylation (introduction of carboxyalkyl group (C)) and cationization (introduction of cationic substituent group (D)). The polyoxyalkylenating reaction, sulfonating reaction, carboxylating reaction and cationizing reaction may be carried out in any order, or 2 to 4 reactions can be carried out simultaneously, but the reactions are carried out preferably in the order of the polyoxyalkylenating reaction, cationizing reaction, carboxylating reaction and sulfonating reaction.

The polysaccharide used in the present invention or a derivative thereof includes polysaccharides such as cellulose, guar gum, starch, pullulan, dextran, fructan, mannan, agar, carrageenan, chitin, chitosan, pectin, alginic acid, hyaluronic acid and inulin, as well as derivatives thereof substituted with a methyl group, ethyl group, hydroxyethyl group, hydroxypropyl group etc. The constituent monosaccharide residue may be substituted with one or more of these substituent groups, and examples of the polysaccharide derivatives include hydroxyethyl cellulose, hydroxyethylethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, hydroxypropylmethyl starch etc. These polysaccharides or derivatives thereof are preferably cellulose, starch, hydroxyethyl cellulose, methyl cellulose, ethyl cellulose and hydroxypropyl cellulose, and particularly hydroxyethyl cellulose is preferable. The substituent group on the polysaccharide derivative can further be substituted with a hydroxy group such as a hydroxyethyl group or hydroxypropyl group to form, for example, a polyoxyethylene chain or the like thereby attaining a substitution degree of higher than 3.0 per substituent monosaccharide residue, and the substitution degree per constituent monosaccharide residue is preferably 0.1 to 10.0, more preferably 0.5 to 5.0. The weight-average molecular weight of the polysaccharide or a derivative thereof is preferably in the range of 1000 to 10000000, more preferably 10000 to 5000000, even more preferably 10000 to 2000000.

Hereinafter, the polyoxyalkylenating reaction, sulfonating reaction, carboxylating reaction and cationizing reaction are described respectively in more detail.

(Polyoxyalkylenating Reaction)

The polyoxyalkylenating reaction of the polysaccharide or a derivative thereof is carried out by dissolving or dispersing the polysaccharide or a derivative thereof in a suitable solvent and reacting it with the polyoxyalkylenating agent (a) represented by the formula (3p) above.

Among the groups represented by $E^3$ in the formula (3p), the C3 to C6 epoxylated alkyl group includes a 2,3-epoxypropyl group, 3,4-epoxybutyl group, 4,5-epoxypentyl group, 5,6-epoxyhexyl group etc. The C1 to C6 linear or branched halogenated alkyl group whose hydroxy group may be substituted includes a 2-chloroethyl group, 3-chloropropyl group, 4-chlorobutyl group, 6-chlorohexyl group, 2-bromoethyl group, 2-hydroxy-3-chloropropyl group, 1-hydroxymethyl-2-chloroethyl group etc. The C2 to C6 carboxyalkyl group includes a carboxymethyl group, carboxyethyl group, carboxypropyl group, carboxybutyl group, carboxypentyl group etc., and derivatives of the carboxyalkyl group or carboxy group include a methyl ester compound, ethyl ester compound, acid halide, tosylated compound, mesylated compound, anhydride etc. Preferable examples of E3 include a 2,3-epoxypropyl group, 2-chloroethyl group, 3-chloropropyl group, 2-hydroxy-3-chloropropyl group, carboxymethyl group, carboxyethyl group, and methyl esters or acid halides thereof.

The polyoxyalkylenating agents (3p) can be used alone or as a mixture of two or more thereof, and the amount used thereof can be regulated suitably depending on the amount of the substituent groups (A) introduced into the polysaccharide and a derivative thereof, and usually the amount of the polyoxyalkylenating agent used is preferably in the range of 0.0001 to 10 equivalents, particularly 0.00015 to 5 equivalents, per constituent monosaccharide residue of the polysaccharide or a derivative thereof.

This reaction is carried out, as needs arise, preferably in the presence of an alkali or an acid, and such alkali includes group 1 or 2 element hydroxides, carbonates, bicarbonates, tertiary amines etc., among which sodium hydroxide, potassium hydroxide, calcium hydroxide, magnesium hydroxide and pyridine are preferable. To give an excellent result, the amount of the alkali used is preferably in 1.0- to 10-molar excess, more preferably 1.05- to 5.0-molar excess, relative to the polyoxyalkylenating agent (3p) used. The acid includes mineral acids, organic acids etc., among which sulfuric acid, hydrochloric acid, p-toluenesulfonic acid and methanesulfonic acid are preferable. To give an excellent result, the molar ratio of the acid to the polyoxyalkylenating agent used is preferably in the range of 0.01 to 0.5, more preferably 0.1 to 0.3.

The solvent includes lower alcohols such as isopropyl alcohol, tert-butyl alcohol etc. A mixed solvent having preferably 0.1 to 100 wt %, more preferably 1 to 90 wt %, water added to a lower alcohol may be used for the purpose of increasing the reactivity between the polysaccharide or a derivative thereof and the polyoxyalkylenating agent (3p).

The reaction temperature is preferably in the range of 0 to 150° C., more preferably 30 to 100° C. After the reaction is finished, the reaction mixture can be neutralized with an acid or alkali. The acid includes inorganic acids such as sulfuric acid, hydrochloric acid and phosphoric acid and organic acids such as acetic acid, and the alkali includes group 1 or 2 element hydroxides such as sodium hydroxide, potassium hydroxide and magnesium hydroxide. The subsequent reaction can also be carried out without neutralization.

(Sulfonating Reaction)

The sulfonating reaction of the polysaccharide or a derivative thereof is carried out by dissolving or dispersing the polysaccharide or a derivative thereof in a suitable solvent and reacting it with the sulfonating agent (b).

In the sulfonating agent (b), the substituent halogen atom in the C1 to C5 haloalkanesulfonic acid whose hydroxy group may be substituted includes a fluorine atom, chlorine atom, bromine atom etc., and salts thereof include salts with the group 1 or 2 elements such as a sodium salt, potassium salt, calcium salt, magnesium salt etc., as well as ammonium salts. The sulfonating agent is preferably vinylsulfonic acid, 3-halo-2-hydroxypropanesulfonic acid, 3-halopropanesulfonic acid, or 2,3-epoxypropanesulfonic acid, and these sulfonating agents can be used alone or as a mixture of two or more thereof, and the amount of the sulfonating agent used can be suitably regulated depending on a desired amount of the sulfonic acid groups (B) introduced into the polysaccharide or a derivative thereof, but is usually preferably in the range of 0 to 10 equivalents, more preferably 0 to 2 equivalents, per constituent monosaccharide residue of the polysaccharide or a derivative thereof.

Preferably the sulfonating reaction is carried out if necessary in the presence of an alkali, and such alkali includes group 1 or 2 element hydroxides, carbonates, bicarbonates etc., among which sodium hydroxide, potassium hydroxide, calcium hydroxide and magnesium hydroxide are preferable. To give an excellent result, the amount of the alkali used is preferably in 0.1- to 3.0-molar excess, more preferably 0.5- to 1.5-molar excess, relative to the sulfonating agent used.

The solvent includes lower alcohols such as isopropyl alcohol, tert-butyl alcohol etc. A mixed solvent having preferably 0.1 to 90 wt %, more preferably 1 to 50 wt %, water added to a lower alcohol may be used for the purpose of increasing the reactivity between the polysaccharide or a derivative thereof and the sulfonating agent.

The reaction temperature is preferably in the range of 0 to 150° C., more preferably 30 to 100° C. After the reaction is finished, the alkali can be neutralized with an acid if necessary. The acid includes inorganic acids such as sulfuric acid, hydrochloric acid and phosphoric acid and organic acids such as acetic acid. Alternatively, the subsequent reaction can be carried out without neutralization.

(Carboxylation)

The carboxylating reaction of the polysaccharide or a derivative thereof is carried out by dissolving or dispersing the polysaccharide or a derivative thereof in a suitable solvent and reacting it with the carboxylating agent (c) in the presence of an alkali.

The carboxylating agent (c) is specifically monochloroacetic acid, sodium monochloroacetate, potassium monochloroacetate, sodium monobromoacetate, potassium monobromoacetate etc. These carboxylating agents (c) can be used alone or as a mixture of two or more thereof, and the amount of the carboxylating agent (c) used can be suitably regulated depending on a desired amount of the carboxyalkyl groups (C) introduced into the polysaccharide or a derivative thereof, but is usually preferably in the range of 0 to 10 equivalents, more preferably 0 to 1 equivalent, per constituent monosaccharide residue of the polysaccharide or a derivative thereof.

The alkali used in this reaction includes sodium hydroxide, potassium hydroxide, calcium hydroxide and magnesium hydroxide. The amount of the alkali used is preferably in 1.0- to 3.0-molar excess, more preferably 1.05- to 2.5-molar excess, relative to the carboxylating agent (c) used. An amount of the alkali outside the above range is not preferable because when the amount of the alkali is too low, the reaction rate is decreased, while when the amount is too high, decomposition of the polysaccharide or a derivative thereof occurs easily.

The solvent includes isopropyl alcohol, tert-butyl alcohol etc. Usually, a mixed solvent having 1 to 90 wt % water added to isopropyl alcohol or tert-butyl alcohol is used for the purpose of increasing the reactivity with the polysaccharide or a derivative thereof and the carboxylating agent (c).

The reaction temperature is preferably in the range of 0 to 150° C., more preferably 30 to 100° C. After the reaction is finished, the alkali can be neutralized with an acid if necessary. The acid includes inorganic acids such as sulfuric acid, hydrochloric acid and phosphoric acid and organic acids such as acetic acid. Alternatively, the subsequent reaction can be carried out without neutralization.

(Cationizing Reaction)

The cationizing reaction of the polysaccharide or a derivative thereof is carried out by dissolving or dispersing the polysaccharide or a derivative thereof in a suitable solvent and reacting it with the cationizing agent (d).

Among the groups represented by $D^2$ in the formula (4p), the C3 to C6 epoxylated alkyl group includes a 2,3-epoxypropyl group, 3,4-epoxybutyl group, 4,5-epoxypentyl group, 5,6-epoxyhexyl group etc. The C1 to C6 linear or branched halogenated alkyl group whose hydroxy group may be substituted includes a 2-chloroethyl group, 3-chloropropyl group, 4-chlorobutyl group, 6-chlorohexyl group, 2-bromoethyl group, 2-hydroxy-3-chloropropyl group, 1-hydroxymethyl-2-chloroethyl group etc. Preferable examples of D2 include a 2,3-epoxypropyl group, 2-chloroethyl group, 3-chloropropyl group, 2-hydroxy-3-chloropropyl group etc. These cationizing agents (d) can be used alone or as a mixture of two or more thereof, and the amount of the cationizing agent (d) used can be regulated suitably depending on the desired amount of the cationic substituent groups (D) introduced into the polysaccharide and a derivative thereof, but is usually preferably in the range of 0 to 10 equivalents, particularly 0 to 5 equivalents, per constituent monosaccharide residue of the polysaccharide or a derivative thereof.

Preferably this reaction is carried out if necessary in the presence of an alkali, and such alkali includes group 1 or 2 element hydroxides, carbonates, bicarbonates etc., among which sodium hydroxide, potassium hydroxide, calcium hydroxide, magnesium hydroxide etc. are preferable. To give an excellent result, the amount of the alkali used is preferably in 1.0- to 3.0-molar excess, more preferably 1.05- to 1.5-molar excess, relative to the cationizing agent (d) used.

The solvent includes lower alcohols such as isopropyl alcohol, tert-butyl alcohol etc. A mixed solvent having preferably 0.1 to 100 wt %, more preferably 1 to 90 wt %, water added to a lower alcohol may be used for the purpose of increasing the reactivity between the polysaccharide or a derivative thereof and the cationizing agent (d).

The reaction temperature is preferably in the range of 0 to 150° C., more preferably 30 to 100° C. After the reaction is finished, the alkali can be neutralized with an acid. The acid includes inorganic acids such as sulfuric acid, hydrochloric acid and phosphoric acid and organic acids such as acetic acid. The subsequent reaction can also be carried out without neutralization.

When the polysaccharide derivative obtained in the respective reactions described above is used subsequently in other reaction, the reaction mixture can be used as it is without neutralization, and if necessary, the reaction mixture can be used after separation by filtration or the like or after washing with hot water, water-containing isopropyl alcohol, water-containing acetone etc. to remove the unreacted compound (a), (b), (c) or (d) or salts formed as byproducts by neutralization etc. When introduction of the objective substituent group is finished, the reaction mixture can be neutralized, separated by filtration etc. and washed if necessary, followed by drying to give the polysaccharide derivative of the present invention.

The thus obtained polysaccharide derivative of the present invention is excellent in water solubility and useful as an emulsifier having an excellent emulsifying action to allow a hydrophobic compound to be extremely stably present in water. Accordingly, an aqueous composition containing the polysaccharide derivative of the present invention, when a hydrophobic compound is present, allows the hydrophobic compound to be extremely stably present by the emulsifying, dispersing and protective colloidal action of the polysaccharide derivative.

This aqueous polysaccharide derivative composition containing a hydrophobic compound does not undergo a change with time or a change in viscosity or a change in outward appearance such as separation, by adding a generally used surfactant, and releases the hydrophobic compound efficiently when used, and is thus extremely useful in the toiletry field. The hydrophobic compound includes higher alcohols, sterols, silicones, fluorine-based oils, oily components etc. to improve the function and added value of toiletry products.

The content of the polysaccharide derivative in the aqueous composition is preferably 0.01 to 5 wt %, more preferably 0.05 to 2 wt %. When the hydrophobic compound is added, its amount is preferably 0.0001 to 50 wt %, more preferably 0.001 to 30 wt %.

A surfactant, dispersant, solvent, perfume, dye, inorganic salt and pH adjusting agent used usually in toiletry products can be arbitrarily added to the aqueous composition containing the polysaccharide derivative of the present invention.

The polysaccharide derivative of the present invention and an aqueous composition containing the same can be used in various toiletry products such as a bathing agent, massage cosmetics, a shower agent, a skin care agent, a hair washing agent, a body washing agent, a washing agent for clothing, a finishing agent for clothing and a washing agent for hard surface.

According to the present invention, allergen on a surface and in space can be reduced, and allergen can be particularly efficiently removed.

EXAMPLES

The following examples describe the practice of the present invention. The Examples are mere illustration of the present invention and are not intended to limit the present invention.

Example 1

Compounds A1 to M shown in Table 1 and ACULYN® 22 were used to prepare sample solutions containing 0.01 wt % Compounds A1 to M and 15 wt % ethanol (special grade, SIGMA), the balance being water. These sample solutions were examined for the degree of residual activity of mite allergen R by the following QAS method. The results are shown in Table 1.

TABLE 1

| Sample | Degree of residual activity of mite (%) |
| --- | --- |
| Compound A1 solution | 35 |
| Compound A2 solution | 40 |
| Compound B solution | 50 |
| Compound C solution | 46 |
| Compound D solution | 50 |
| Compound E solution | 46 |
| Compound F solution | 32 |
| Compound G solution | 28 |
| Compound H solution | 32 |
| Compound I solution | 26 |
| Compound J solution | 28 |
| Compound K solution | 42 |
| Compound L solution | 48 |
| Compound M solution | 40 |
| ACULYN® 22 (ISP Ltd.) | 36 |
| Ion exchange water | 100 |
| 15% Aqueous ethanol (standard) | 100 |

ACULYN® 22 is an acrylic acid/alkyl methacrylate/polyoxyethylene (average number of moles added: 20) stearyl ether copolymer available from ISP Ltd.

When compound K was dissolved, acetic acid was used as a pH adjusting agent, and the final pH was 5.5. When ACULYN® 22 was dissolved, sodium hydroxide was used as a pH adjusting agent, and the final pH was 8.0. For the other compounds, a pH adjusting agent was not used, and the pH values of their solutions were in the range of 7 to 8. These pH values are those at 20° C.

Evaluation of Degree of Residual Activity of Mite Allergen by QAS Method

1. An allergen stick of an antigen-specific IgE antibody detection reagent Qiedel Allergy Screen QAS-IV (FUJI REBIO INC.) is impregnated with 100 µl sample solution and left in a moistened box at room temperature for 2 hours.
2. The allergen stick is washed for 30 seconds with physiological saline (Ohtsuka Pharmaceutical Co., Ltd.). Thereafter, the allergen stick is impregnated with 50 µl serum derived from blood of a patient with mite allergy, and then left in a moistened box at room temperature for 18 hours thereby reacting antigen-specific IgE antibody in the blood with antigen.
3. The allergen stick is washed for 20 seconds with physiological saline and then the allergen stick is dipped for 30 minutes at room temperature in a test tube filled with an enzyme-labeled antibody solution (containing 0.0075 mg/mL alkali phosphatase-labeled anti-IgE antibody (mouse), included in QAS kit), to form an antigen/antigen-specific IgE antibody/enzyme-labeled antibody conjugate.
4. The allergen stick is washed with tap water for 2 minutes, and then the allergen stick is colored by dipping it for 1 hour at room temperature in a test tube filled with a substrate solution (containing 2.16 mg/mL 5-bromo-4-chloro-3-indolyl phosphate, attached to QAS kit).
5. The allergen stick is scanned by an image scanner (Sharp JX350), and the coloration of a *Dermatophagoides farinae* part and a *Dermatophagoides ptemysinus* part in an incorporated image is quantified by Lane & Spot Analyzer (ATTO Corporation). The quantification value shall be regarded to be higher as the color density is increased.

As the negative control stick, an allergen stick impregnated with 15 wt % aqueous ethanol is subjected to the same operation as described above. The coloration of the *Dermatophagoides farinae* part in the negative control stick is Rt, the coloration of the negative control part is Rr, the coloration of the *Dermatophagoides farinae* part in the stick impregnated with the test solution is Dt, and the coloration of the negative control part is Dr, and (Dt−Dr)/(Rt−Rr)×100 is the degree of residual activity of mite allergen Rf (%) for *Dermatophagoides farinae* allergen. Similarly, the *Dermatophagoides ptemysinus* part is also examined to determine the degree of residual activity of mite allergen Rp (%) for *Dermatophagoides ptemysinus* allergen by the same calculation. The mean value of Rf and Rp is regarded as the degree of residual activity of mite allergen R (%).

Example 2

Space with a floor area of 7.4 m² and a height of 2.3 m (capacity 17 m², temperature 23° C.) was sealed, and a cotton futon actually used for 2 years in home was given with an impact for 10 seconds with a futon beater to generate dust in the space and stir up the dust. Then, 17 g of the allergen-reducing agent in Table 2 was sprayed into the space upward at a direction of 45° from a height of 1.7 meters over the floor by using a trigger-type spray (trigger attached to ALERUCLEAN Cleaning Spray for futon, manufactured by Kao Corporation).

Thirty minutes after spraying, a high-volume air sampler (HV-500F, Shibata Scientific Technology Ltd.) equipped with a glass fiber filter (GB-100R-110A, Shibata Scientific Technology Ltd.) was operated under the condition of 500 L/min. for 60 minutes on the floor, to capture dust on the filter. The glass fiber filter on which the dust had been captured was squeezed in 1 cc or less solution containing PBS (phosphate buffer solution, pH 7.4±0.1 (that is, a solution of 0.144 g/L $KH_2PO_4$, 9.00 g/L NaCl and 0.795 g/L $Na_2HPO_4.7H_2O$ in distilled water, containing 0.05 wt % Tween 20 (SIGMA), hereinafter, referred to as T-PBS) to extract allergen from the dust, and the concentration of Der f II in the extract was colored by sandwich ELISA.

Coloration without spraying was compared with coloration with spraying to evaluate the effect of the spraying on reduction of allergen.

A test without spraying and a test of each allergen-reducing agent in Table 2 were carried out one after another and repeated 4 times in a suitable different order, and when the allergen reducing effects examined 4 times were compared, all of the allergen-reducing agents in the formulation examples in Table 2 exhibited an excellent allergen reducing effect. Formulation Examples 3 to 5 and Formulation Examples 10 to 15 gave a particularly excellent reducing effect. The results of all the formulation examples were superior to those of the tests carried out separately by spraying water only.

Example 3

Space with a floor area of 7.4 m² and a height of 2.3 m (capacity 17 m², temperature 23° C.) was sealed, and a cotton futon actually used for 2 years in home was given with an impact for 10 seconds with a futon beater to generate dust in the space and stir up the dust.

After 3 hours, the floor surface was cleaned at 20 seconds/m² with a vacuum-cleaner (CV-CD4, suction power of 530 W, manufactured by Hitachi, Ltd.). Immediately thereafter, a sheet structure A wherein a nonwoven fabric obtained by a method of preparing a nonwoven fabric as shown below was impregnated at an impregnation degree of 250% (ratio by weight) with the allergen-reducing agent in Table 2 was fitted in Quickie Wiper (Kao Corporation) and used to wipe the floor surface.

After wiping, the floor surface was left for 3 hours and then wiped the whole floor surface with a wiping sheet B having a commercial cleaning sheet (Floor Quickie Dry Type, Kao Corporation) impregnated at an impregnation degree of 150% (ratio by weight) with T-PBS.

From the sheet B, the contaminated PBS was squeezed out and colored by sandwich ELISA shown below.

The coloration in a test (control test) of sheet A impregnated with water in place of the allergen-reducing agent in Table 2 was compared with the coloration of sheet A impregnated with the composition shown in Table 2, to evaluate the effect of reducing allergen.

The control test and the test of the allergen-reducing agent in Table 2 were carried out one after another and repeated 4 times in a suitable different order, and when the effects of the allergen reducing effect examined 4 times were compared, all of the allergen-reducing agents in the formulation examples in Table 2 exhibited an allergen reducing effect superior to that of the control test. Formulation Examples 3 to 5 and Formulation Examples 10 to 15 gave a particularly excellent reducing effect.

Example 4

Space with a floor area of 7.4 $m^2$ and a height of 2.3 m (capacity 17 $m^2$, temperature 23° C.) was sealed, and a cotton futon actually used for 2 years in home was given with an impact for 10 seconds with a futon beater to generate dust in the space and stir up the dust.

After 3 hours, a sheet structure A wherein a nonwoven fabric obtained by a method of preparing a nonwoven fabric as shown below was impregnated at an impregnation degree of 250% (ratio by weight) with the allergen-reducing agent in Table 2 was fitted in a wiper device (Quickle Wiper, Kao Corporation) and used to wipe the floor surface. Immediately thereafter, the floor surface was cleaned at 20 seconds/$m^2$ with a vacuum-cleaner (CV-CD4, suction power of 530 W, Hitachi, Ltd.).

After wiping, the floor surface was left and then wiped the whole floor surface with a wiping sheet B having a commercial cleaning sheet (Floor Quickle Dry Type, Kao Corporation) impregnated at an impregnation degree of 150% (ratio by weight) with T-PBS.

From the sheet B, the contaminated PBS was squeezed out and colored by sandwich ELISA shown below.

The coloration in a test (control test) of the sheet impregnated with water in place of the allergen-reducing agent in Table 2 was compared with the coloration of the sheet impregnated with the allergen-reducing agent shown in Table 2, to evaluate the effect of reducing allergen.

The control test and the test of the allergen-reducing agent in Table 2 were carried out one after another and repeated 4 times in a suitable different order, and when the effects of the allergen reducing effect examined 4 times were compared, all of the allergen-reducing agents in the formulation examples in Table 2 exhibited an excellent allergen reducing effect. Formulation Examples 3 to 5 and Formulation Examples 10 to 15 gave a particularly excellent reducing effect.

The reducing degrees were higher than those in Example 3 where the corresponding formulations were used.

Example 5

Space with a floor area of 7.4 $m^2$ and a height of 2.3 m (capacity 17 $m^2$, temperature 23° C.) was sealed, and a cotton futon actually used for 2 years in home was given with an impact for 10 seconds with a futon beater to generate dust in the space and stir up the dust.

After 3 hours, 30 g of the allergen-reducing agent in Table 2 was sprayed into space downward at a direction of 45° from a height of 0.6 m over the floor by using a trigger-type spray (trigger attached to ALERUCLEAN Cleaning Spray for futon, manufactured by Kao Corporation). Immediately thereafter, 4 nonwoven fabrics obtained by a method of preparing a nonwoven fabric as shown below, which were fitted in Quickie Wiper (Kao Corporation), were used one after another to clean the floor surface.

After 3 hours, the floor surface was wiped with a wiping sheet B having a commercial cleaning sheet (Floor Quickle Dry Type, Kao Corporation) impregnated at an impregnation degree of 150% (ratio by weight) with T-PBS.

From the sheet B, the contaminated PBS was squeezed out and colored by sandwich ELISA shown below.

The coloration in a test (control test) by spraying water in place of the allergen-reducing agent in Table 2 was compared with the coloration in a test by spraying the allergen-reducing agent shown in Table 2, to evaluate the effect of reducing allergen.

The control test and the test of the allergen-reducing agent in Table 2 were carried out one after another and repeated 4 times in a suitable different order, and when the effects of the allergen reducing effect examined 4 times were compared, all of the allergen-reducing agents in the formulation examples in Table 2 exhibited a more excellent allergen reducing effect. Formulation Examples 3 to 5 and Formulation Examples 10 to 15 gave a particularly excellent reducing effect.

<Sandwich ELISA Method>

1. Monoclonal antibody 15E11 (Seikagaku Corporation) is diluted at a concentration of 2 μg/ml in PBS (phosphate buffer solution, pH 7.4±0.1 (that is, a solution of 0.144 g/L $KH_2PO_4$, 9.00 g/L NaCl and 0.795 g/L $Na_2HPO_4.7H_2O$ in distilled water), then pipetted into a well (50 μl/well) of a microplate (ELISA PLATE H TYPE, Sumitomo Bakelite Co., Ltd.) and left at room temperature for 2 hours.

2. The plate is washed 3 times with PBS.

3. PBS (Block Ace, Dainippon Pharmaceutical Co., Ltd.) containing 1% BSA (SIGMA) is pipetted into each well (200 μl/well) and left at room temperature for 1 hour for blocking.

4. The plate is washed 3 times with T-PBS (PBS containing 0.05 wt % Tween 20 (SIGMA)).

5. Separately, 0.3 μg/ml rDer f II (Seikagaku Corporation) is diluted 2″-fold with 9-tube T-PBS, and each dilution is pipetted as a standard in a volume of 50 μl into each well, while a well to which 50 μl T-PBS is added as a negative control in place of rDer f II is prepared. The sample to be measured is diluted suitably with T-PBS and pipetted in a volume of 50 μl into each well. The plate is left at room temperature for 2 hours.

6. The plate is washed 3 times with T-PBS.

7. HRP-labeled 13A4 (Seikagaku Corporation) at optimum concentration is pipetted in a volume of 50 μl into each well and left at room temperature for 2 hours.

8. The plate is washed 3 times with T-PBS.

9. A coloration kit T for peroxidase (Sumitomo Bakelite Co., Ltd.) is used in coloration. First, 0.1 ml substrate solution is added to and mixed with 10 mL coloration agent to form a coloration solution. This coloration solution is pipetted in a volume of 100 μl into each well and colored at room temperature. According to this method, higher yellow coloration is indicative of a higher concentration of allergen in the solution.

<Method of Preparing a Nonwoven Fabric>

An air-through nonwoven fabric with a basis weight of 27 g/m² was prepared from low-melting fibers having a core/sheath structure (2.8 dtex×51 mm; the melting point of the sheath component, 130° C.) in a cubic crimped form wherein the core was made of polypropylene and the sheath was made of polyethylene. The fibers were heat-bonded to one another at a temperature of 140° C. The breaking strength of the air-through nonwoven fabric was 1660 cN/25 mm in the machine direction (MD) and 220 cN/25 mm in the crosswise direction (CD).

Separately, rayon fibers (1.7 dtex×40 mm), acrylic fibers (0.9 dtex×51 mm), and core/sheath fibers (1.0 dtex×38 mm), having polypropylene as the core and polyethylene as the sheath, were mixed at a ratio of 50/25/25 by weight. A fiber web having a basis weight of 19 g/m² was prepared with a card machine, using an ordinary method. The air-through nonwoven fabric was sandwiched between the fiber webs thus obtained. The resulting product was subjected to water needling under low-energy conditions, and the air-through nonwoven fabric and the fiber webs were interweaved with one another to prepare a composite spunlace nonwoven fabric with a basis weight of 65 g/m² having a surface layer with high freedom of fibers. Using an ultrasonic embossing machine, the whole surface of the prepared nonwoven fabric was embossed to have an embossed diamond pattern to obtain the nonwoven fabric used in the Examples described above.

TABLE 2

| | | | | Formulation example | | | | | | | |
|---|---|---|---|---|---|---|---|---|---|---|---|
| | | | | 1 | 2 | 3 | 4 | 5 | 6 | 7 | 8 |
| Allergen reducing agent | Compounding ingredients (wt %) | (a) | Compound A1 | 0.1 | 0.1 | 0.1 | | | | | |
| | | | Compound A2 | | | | 0.1 | 0.2 | 0.1 | | |
| | | | Compound B | | | | | | 0.1 | 0.1 | |
| | | | Compound C | | | | | | | 0.1 | |
| | | | Compound D | | | | | | | | 0.1 |
| | | | Compound E | | | | | | | | |
| | | | Compound F | | | | | | | | |
| | | | Compound G | | | | | | | | |
| | | | Compound H | | | | | | | | |
| | | | Compound I | | | | | | | | |
| | | | Compound J | | | | | | | | |
| | | | ACULYN® 22 (ISP Ltd.) | | | | | | | | |
| | | (b) | Water | Balance | Balance | Balance | Balance | Balance | Balance | Balance | Balance |
| | | (c) | Ethanol | 3.0 | 5.0 | 5.0 | 3.0 | 2.0 | 5.0 | 5.0 | 5.0 |
| | | | Isopropanol | | | | 1.0 | 2.0 | | | |
| | | (d) | Dihydrojasmone | 0.05 | | | 0.05 | 0.05 | | | |
| | | | Methyl dihydrojasmonate | | 0.05 | 0.05 | 0.05 | 0.05 | 0.05 | 0.05 | 0.05 |
| | | (e) | Benzalkonium chloride | 0.01 | | | | 0.01 | | | |
| | | | Polylysine | | 0.02 | 0.02 | 0.02 | | | | |
| | | | Sodium sulfate | | | 0.2 | 0.2 | 0.2 | | | |
| | | | Propyleneglycol monomethyl ether | | | 1.0 | 1.0 | 1.0 | | | |
| | | | Total | 100 | 100 | 100 | 100 | 100 | 100 | 100 | 100 |
| | pH(20° C.) | | | 7 | 7 | 7 | 7 | 7 | 7 | 7 | 7 |

| | | | | Formulation example | | | | | | |
|---|---|---|---|---|---|---|---|---|---|---|
| | | | | 9 | 10 | 11 | 12 | 13 | 14 | 15 |
| Allergen reducing agent | Compounding ingredients (wt %) | (a) | Compound A1 | | | | | | | |
| | | | Compound A2 | | | | | | | |
| | | | Compound B | | | | | | | |
| | | | Compound C | | | | | | | |
| | | | Compound D | | | | | | | |
| | | | Compound E | 0.1 | | | | | | |
| | | | Compound F | | | 0.1 | | | | |
| | | | Compound G | | | | 0.1 | | | |
| | | | Compound H | | | | | 0.1 | | |
| | | | Compound I | | | | | | 0.1 | |
| | | | Compound J | | | | | | | 0.1 |
| | | | ACULYN® 22 (ISP Ltd.) | | 0.1 | | | | | |
| | | (b) | Water | Balance | Balance | Balance | Balance | Balance | Balance | Balance |
| | | (c) | Ethanol | 5.0 | 5.0 | 5.0 | 5.0 | 5.0 | 5.0 | 5.0 |
| | | | Isopropanol | | | | | | | |
| | | (d) | Dihydrojasmone | | | | | | | |
| | | | Methyl dihydrojasmonate | 0.05 | 0.05 | | | | | |
| | | (e) | Benzalkonium chloride | | | | | | | |
| | | | Polylysine | | | | | | | |
| | | | Sodium sulfate | | | | | | | |
| | | | Propyleneglycol monomethyl ether | | | | | | | |
| | | | Total | 100 | 100 | 100 | 100 | 100 | 100 | 100 |
| | pH(20° C.) | | | 7 | 7 | 7 | 7 | 7 | 7 | 7 |

Compounds A1, A2, B, C, D, E, F, G, H, I and J in Table 2 were obtained by the Synthesis Examples below. Aculyn 22 is a polymer compound from ISP Ltd., that is, an acrylic acid/alkyl methacrylate/polyoxyethylene (average number of moles added: 20) stearyl ether copolymer. In the table, the pH value was regulated by using sulfuric acid and aminomethyl propanol as the pH adjusting agent.

Synthesis Example 1

Compound A1

80 g of hydroxyethyl cellulose (HEC-QP100 MH, manufactured by Union Carbide) having a weight-average molecular weight of 1,500,000 and a hydroxyethyl group substitution degree of 1.8, 640 g of 80% aqueous isopropyl alcohol (IPA) and 5.34 g of 48% aqueous sodium hydroxide solution were mixed to prepare slurry and stirred at room temperature for 30 minutes in a nitrogen atmosphere. To this solution was added to 12.78 g polyoxyalkylene compound represented by the following formula:

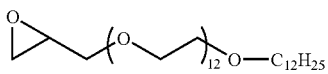

The mixture was reacted at 80° C. for 8 hours for polyoxyalkylenation. After the reaction was finished, the reaction solution was neutralized with acetic acid, and the reaction product was separated by filtration. The reaction product was washed twice with 500 g isopropyl alcohol and dried at 60° C. under reduced pressure for 1 day to give 72 g compound A1. The degree of substitution of the polyoxyalkylene group was 0.004.

Synthesis Example 2

Compound A2

According to methods described in Synthesis Example 1 and WO00/73351, hydroxyethyl cellulose having a weight-average molecular weight of 200,000 and a hydroxyethyl group substitution degree of 2.5 (manufactured by Hercules Incorporated) was used, and a polyoxyalkylene compound represented by the following formula was added thereto to give compound A2 having a polyoxyalkylene group substitution degree of 0.014.

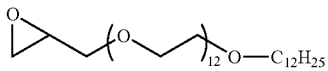

Synthesis Example 3

Compound B 20 g polyvinyl alcohol having an average polymerization degree of 2000, 200 g dimethyl sulfoxide (DMSO), and 1.81 g granular NaOH were mixed and stirred at 70° C. When the solution became uniform, it was cooled. 1.87 g compound represented by the following formula:

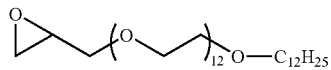

was added at room temperature. The mixture was aged at 80° C. for 8 hours. After cooling, the reaction solution was neutralized with 2.59 mL acetic acid. The reaction product was added to IPA. Precipitated white solids were filtered and the resulting solids were washed with IPA (300 mL×3). After drying under reduced pressure, 19.0 g compound B having the following unit shown below was obtained.

—CH$_2$CH—CH$_2$CH—
     |            |
    OH      O

HO—

O$\diagdown$$\diagup$$\diagdown$(O$\diagdown$$\diagup$)$_{10}$O$\diagdown$$\diagup$O—C$_{12}$H$_{25}$ The degree of substitution of the substituent group including the polyoxyalkylene group in the resulting compound B was 0.0033.

Synthesis Example 4

Compound C

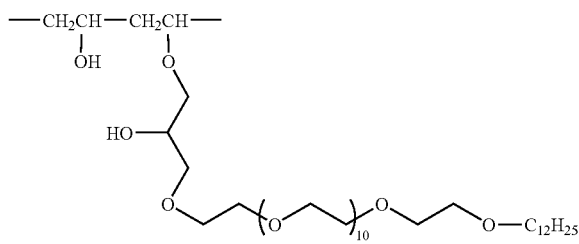

97.1 g monomer A and 20.7 g monomer B in the above scheme and 180 g ethanol were mixed. The reaction system was degassed by blowing a nitrogen gas into the solution (20 mL/min., 1 hour) and then heated to 60° C. Thereafter, 82.8 g solution of V-65 (azo polymerization initiator, Wako Pure Chemical Industries, Ltd.) in ethanol (3 wt %) was added dropwise to it while the temperature was kept at 60° C. After dropping, the mixture was aged at 60° C. for 12 hours. After the reaction was finished, the resulting reaction product was added dropwise to 2 kg diisopropyl ether. The resulting white solids were separated by filtration and washed with diisopropyl ether (500 g×twice). After drying under reduced pressure, 105 g compound C was obtained. The degree of introduction of the monomer B in the resulting compound C, as determined by NMR, was 0.025. The weight-average molecular weight was 51000.

Synthesis Example 5

Compound D

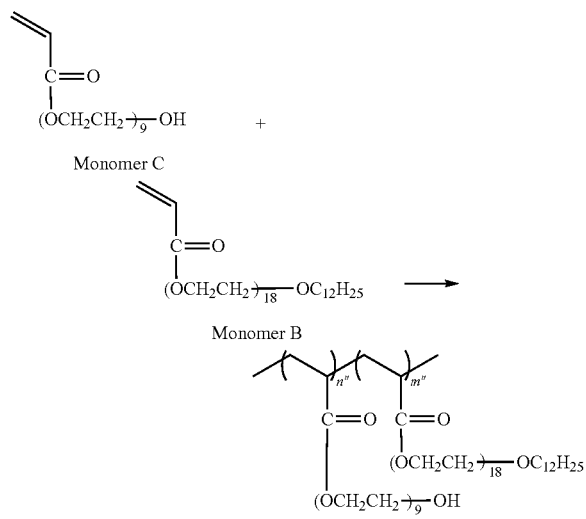

Monomer C

Monomer B 501.8 g monomer C and 20.7 g monomer B in the above scheme and 780 g ethanol were mixed. The reaction system was degassed by blowing a nitrogen gas into the solution (40 mL/min., 1 hour) and then heated to 60° C. Thereafter, 82.8 g V-65 ethanol solution (3 wt %) was dropped to it while the temperature was kept at 60° C. After dropping, the mixture was aged at 60° C. for 12 hours. After the reaction was finished, the resulting reaction product was added dropwise to 5 kg diisopropyl ether. The resulting white solids were separated by filtration and washed with diisopropyl ether (500 g×twice). After drying under reduced pressure, 490 g compound D was obtained. The degree of introduction of the monomer B in the resulting compound ID, as determined by NMR, was 0.022. The weight-average molecular weight was 110000.

Synthesis Example 6

Compound E 3 g polyglycidol having a weight-average molecular weight of 5400, 100 g DMSO, and 0.16 g granular NaOH were mixed and stirred at 70° C. When the solution became uniform, it was cooled. 0.765 g compound represented by the following formula:

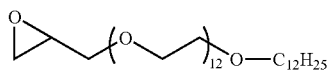

was added thereto at room temperature, and the mixture was aged at 80° C. for 8 hours. After cooling, the reaction solution was neutralized with 0.23 mL acetic acid. DMSO was distilled away, and the resulting pale yellow viscous solid was washed with IPA (30 mL×3). After drying under reduced pressure, 2.9 g compound E having the unit shown below was obtained.

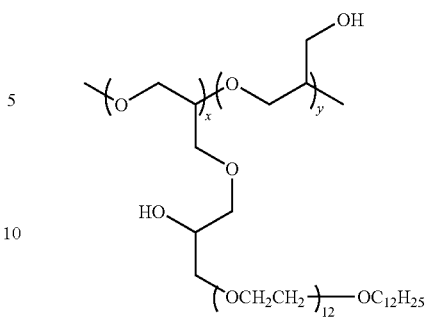

The degree of substitution of the substituent group including the polyoxyalkylene group in the resulting compound E was 0.0053.

Synthesis Example 7

(Compound F) HEC (200,000)+EO-Cholesteryl (Degree of Substitution 3.3/1000))

Compound (F')

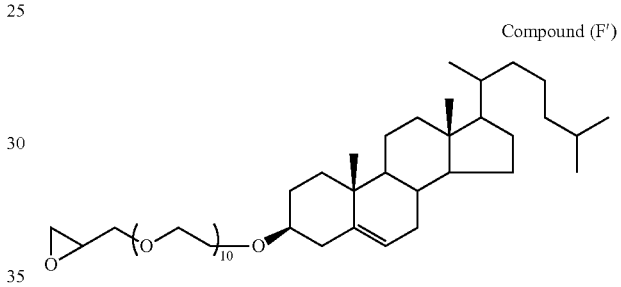

50 g hydroxyethyl cellulose having a weight-average molecular weight of about 200,000 (Natrozol 250G, manufactured by Hercules Incorporated), 225 g isopropyl alcohol and 40 g ion exchange water were mixed and stirred at room temperature for 1 hour in a nitrogen stream. 5.59 g compound (F') and 3.06 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The reaction mixture was filtered, and the resulting solids were washed twice with 400 g isopropyl alcohol. The resulting reaction product was dried for 1 day under reduced pressure to give 48 g polysaccharide derivative (compound F). The degree of substitution of the cholesteryl group of the resulting polysaccharide derivative was 0.0033.

Synthesis Example 8

(Compound G) HEC (100,000)+EO-Branched Alkyl (Degree of Substitution 7.1/1000))

Compound (G')

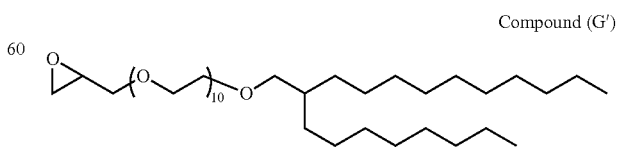

50 g hydroxyethyl cellulose having a weight-average molecular weight of about 100,000 (Natrozol 250LR, manufactured by Hercules Incorporated), 225 g isopropyl alcohol and 25 g ion exchange water were mixed and stirred at room temperature for 1 hour in a nitrogen stream. 8.08 g compound (G') and 3.06 g of 48% aqueous NaOH were added to the solution and heated to 80° C. Thereafter, the mixture was aged at 80° C. for 9 hours. After aging was finished, the reaction solution was cooled to room temperature and neutralized with acetic acid. The reaction mixture was filtered, and the resulting solids were washed twice with 400 g isopropyl alcohol. The resulting reaction product was dried for 1 day under reduced pressure to give 45 g polysaccharide derivative (compound G). The degree of substitution of the octyldodecyl group of the resulting polysaccharide derivative was 0.0071.

Synthesis Example 9

(Compound H) HEC (200,000)+EO-Branched Alkyl (Degree of Substitution 8.6/1000))

Compound (H')

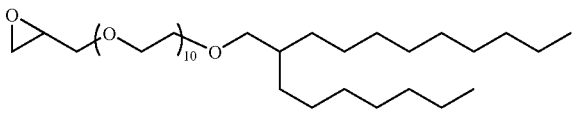

50 g hydroxyethyl cellulose having a weight-average molecular weight of about 200,000 (Natrozol 250G, manufactured by Hercules Incorporated), 225 g isopropyl alcohol and 40 g ion exchange water were mixed and stirred at room temperature for 1 hour in a nitrogen stream. 7.89 g compound (H') and 3.06 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The reaction mixture was filtered, and the resulting solids were washed twice with 400 g isopropyl alcohol. The resulting reaction product was dried for 1 day under reduced pressure to give 47 g polysaccharide derivative (compound H). The degree of substitution of the isostearyl group of the resulting polysaccharide derivative was 0.0086.

Synthesis Example 10

(Compound I) HEC (200,000)+EO-Unsaturated Alkyl (Degree of Substitution 8.1/1000))

Compound (I')

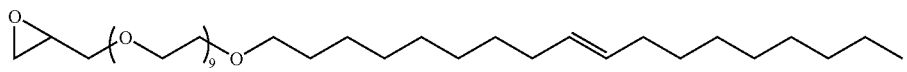

40 g hydroxyethyl cellulose having a weight-average molecular weight of about 200,000 (Natrozol 250G, manufactured by Hercules Incorporated), 180 g isopropyl alcohol and 32 g ion exchange water were mixed and stirred at room temperature for 1 hour in a nitrogen stream. 4.52 g compound (I') and 2.45 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The reaction mixture was filtered, and the resulting solids were washed twice with 400 g isopropyl alcohol. The resulting reaction product was dried for 1 day under reduced pressure to give 38 g polysaccharide derivative (compound I). The degree of substitution of the oleyl group of the resulting polysaccharide derivative was 0.0081.

Synthesis Example 11

(Compound J) Inulin+EO-Lauryl (Degree of Substitution 26.6/1000))

Compound (J')

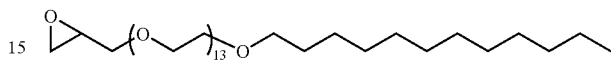

50 g inulin (FujiFF, Fuji nihon seito Corporation), 60 g isopropyl alcohol and 140 g ion exchange water were mixed and stirred at room temperature for 1 hour in a nitrogen stream. 40.8 g compound (J') and 5.14 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The reaction product was added gradually to 2000 g of acetone. The precipitated solids were filtered, and the resulting solids were washed twice with 400 g acetone. The resulting reaction product was dried for 1 day under reduced pressure to give 51 g polysaccharide derivative (compound J). The degree of substitution of the lauryl group of the resulting polysaccharide derivative was 0.0266.

Synthesis Example 12

(Compound K) Chitosan (50,000)+EO-Lauryl (Degree of Substitution 13/1000))

Compound (K')

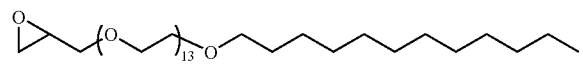

30 g chitosan 10 (manufactured by Wako Pure Chemical Industries, Ltd.), 45 g isopropyl alcohol and 105 g ion exchange water were mixed and stirred at room temperature for 1 hour in a nitrogen stream. 11.84 g compound (K') was added to the solution and heated to 80° C. Thereafter, the mixture was aged at 80° C. for 8 hours. After aging was finished, the reaction solution was cooled to room temperature and neutralized with acetic acid. The resulting reaction mixture was filtered, and the resulting solids were washed twice with 300 g isopropyl alcohol. The resulting reaction product was dried for 1 day under reduced pressure to give 31 g polysaccharide derivative (compound K). The degree of substitution of the lauryl group of the resulting polysaccharide derivative was 0.013.

Synthesis Example 13

(Compound L) Cluster Dextrin+EO-Lauryl (Degree of Substitution 2.4/1000))

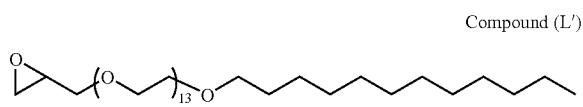

Compound (L')

40 g cluster dextrin (manufactured by Nihon Shokuhin Kako Co., Ltd.), 72 g isopropyl alcohol and 168 g ion exchange water were mixed and stirred at room temperature for 1 hour in a nitrogen stream. 6.53 g compound (L') and 4.11 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The resulting reaction mixture was added gradually to 2000 g acetone. The precipitated solids were filtered, and the resulting solids were washed twice with 400 g isopropyl alcohol. The resulting reaction product was dried for 1 day under reduced pressure to give 39 g polysaccharide derivative (compound L). The degree of substitution of the lauryl group of the resulting polysaccharide derivative was 0.024.

Synthesis Example 14

(Compound M) Guar Gum (50,000)+EO-Lauryl (Degree of Substitution 3.8/1000))

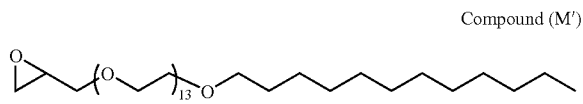

Compound (M')

40 g guar gum having a weight-average molecular weight of about 50,000 (MEYPRO-GUM manufactured by Sansho Co., Ltd.), 40 g isopropyl alcohol and 160 g ion exchange water were mixed and stirred at room temperature for 1 hour in a nitrogen stream. 19.73 g compound (M') and 3.72 g of 48% aqueous NaOH were added to the solution and heated to 80° C. Thereafter, the mixture was aged at 80° C. for 8 hours. After aging was finished, the reaction solution was cooled to room temperature and neutralized with acetic acid. The resulting reaction mixture was filtered, and the resulting solids were washed twice with 400 g isopropyl alcohol. The resulting reaction product was dried for 1 day under reduced pressure to give 32 g polysaccharide derivative (compound M). The degree of substitution of the lauryl group of the resulting polysaccharide derivative was 0.0038.

In Synthesis Examples 15 and 20 below, the degree of substitution of the substituent group (A) in the polysaccharide derivative of the present invention was determined according to the Zeisel method (D. G. Anderson, Anal. Chem., 43, 894 (1971)), and the degrees of substitution of the sulfoalkyl group (B), the carboxyalkyl group (C) and the cationic substituent group (D) were determined by the colloid titration method. In the following examples, the "degree of substitution" refers to the average number of substituent groups per constituent monosaccharide residue.

Synthesis Example 15

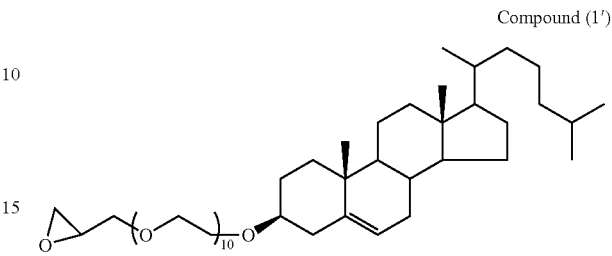

Compound (1')

50 g hydroxyethyl cellulose (Natrozol 250LR having a weight-average molecular weight of about 100,000, manufactured by Hercules Incorporated), 225 g isopropyl alcohol and 25 g ion exchange water were mixed and stirred at room temperature for 1 hour in a nitrogen stream. 8.4 g compound (1') and 3.06 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 45 g cellulose derivative having a polyoxyethylene cholesteryl ether group introduced into it. The degree of substitution of the cholesteryl group of the resulting cellulose derivative was 0.0061.

Synthesis Example 16

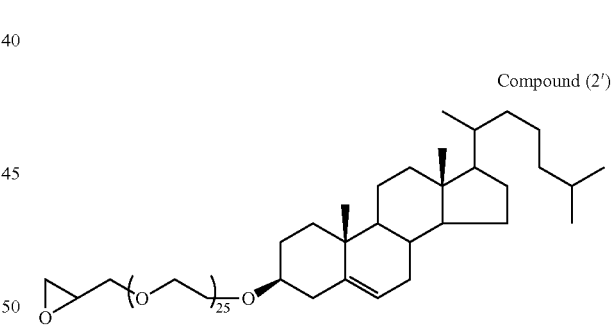

Compound (2')

40 g hydroxyethyl cellulose (Natrozol 250M having a weight-average molecular weight of about 500,000, manufactured by Hercules Incorporated), 260 g isopropyl alcohol and 64 g ion exchange water were mixed and stirred at room temperature for 1 hour in a nitrogen stream. 9.3 g compound (2') and 2.45 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 49 g cellulose derivative having a polyoxyethylene cholesteryl ether group introduced into it. The degree of substitution of the cholesteryl group of the resulting cellulose derivative was 0.0025.

Synthesis Example 17

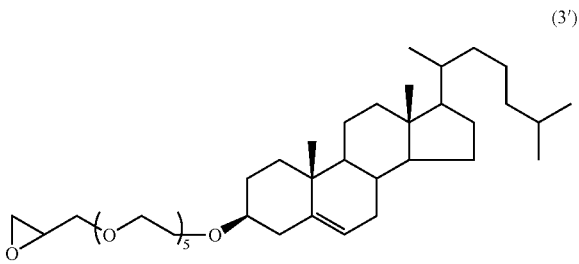

(3')

40 g hydroxyethyl cellulose (Natrozol 250HHX having a weight-average molecular weight of about 1,500,000, manufactured by Hercules Incorporated), 260 g isopropyl alcohol and 64 g ion exchange water were mixed and stirred at room temperature for 1 hour in a nitrogen stream. 3.6 g compound (3') and 2.45 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 46 g cellulose derivative having a polyoxyethylene cholesteryl ether group introduced into it. The degree of substitution of the cholesteryl group of the resulting cellulose derivative was 0.0031.

Synthesis Example 18

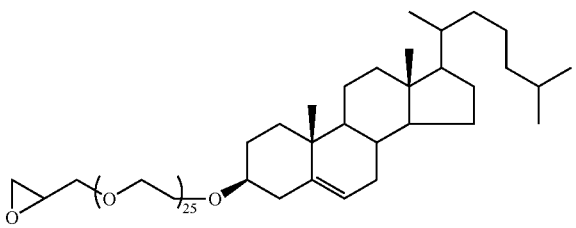

80 g potato starch (manufactured by Katayama Chemical Inc.), 320 g isopropyl alcohol and 320 g ion exchange water were mixed and stirred at room temperature for 1 hour in a nitrogen stream. 14.0 g compound (2') and 5.5 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 76 g starch derivative having a polyoxyethylene cholesteryl ether group introduced into it. The degree of substitution of the polyoxycholesteryl group of the resulting starch derivative was 0.0045.

30 g of the resulting starch derivative, 75 g isopropyl alcohol and 75 g ion exchange water were mixed and stirred at room temperature for 1 hour in a nitrogen stream. 4.33 g sodium 3-chloro-2-hydroxypropanesulfonate and 3.67 g of 48% aqueous NaOH were added to the solution and stirred for 3 hours at 50° C. After stirring was finished, the reaction mixture was cooled to room temperature and neutralized with acetic acid. The reaction product was separated by filtration, and the resulting reaction product was washed twice with 180 g of 50% isopropyl alcohol and twice with 200 g of isopropyl alcohol. The resulting cake was dried for 1 day under reduced pressure to give 28 g starch derivative having a polyoxyethylene cholesteryl ether group and a sulfonate group introduced into it. The degrees of substitution of the cholesteryl group and sulfonate group of the resulting starch derivative were 0.0045 and 0.11, respectively.

Synthesis Example 19

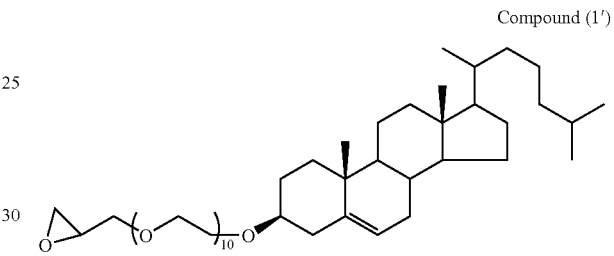

Compound (1')

40 g hydroxyethyl cellulose (Natrozol 250M having a weight-average molecular weight of about 500,000, manufactured by Hercules Incorporated), 260 g isopropyl alcohol and 64 g ion exchange water were mixed and stirred at room temperature for 1 hour in a nitrogen stream. 11.2 g compound (1') and 2.45 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 48 g cellulose derivative having a polyoxyethylene cholesteryl ether group introduced into it. The degree of substitution of the polyoxycholesteryl group of the resulting cellulose derivative was 0.0053.

30 g of the resulting cellulose derivative, 147 g isopropyl alcohol and 63 g ion exchange water were mixed and stirred at room temperature for 1 hour in a nitrogen stream. 4.154 g (3-chloro-2-hydroxy-n-propyl)trimethyl ammonium chloride and 3.67 g of 48% aqueous NaOH were added to the solution and stirred for 3 hours at 50° C. After stirring was finished, the reaction mixture was cooled to room temperature and neutralized with acetic acid. The reaction product was separated by filtration, and the resulting reaction product was washed twice with 180 g of 70% isopropyl alcohol. The resulting cake was dried for 1 day under reduced pressure to give 30 g cellulose derivative having a polyoxyethylene cholesteryl ether group and a cation group introduced into it. The degrees of substitution of the cholesteryl group and cation group of the resulting cellulose derivative were 0.0053 and 0.13, respectively.

Synthesis Example 20

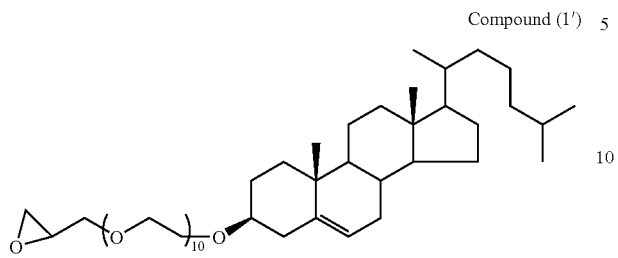

Compound (1′)

40 g hydroxyethyl cellulose (Natrozol 250M having a weight-average molecular weight of about 500,000, manufactured by Hercules Incorporated), 260 g isopropyl alcohol and 64 g ion exchange water were mixed and stirred at room temperature for 1 hour in a nitrogen stream. 11.2 g compound (1') and 2.45 g of 48% aqueous NaOH were added to the solution and stirred for 20 minutes in a nitrogen stream at room temperature. Thereafter, the mixture was heated to 80° C. and reacted for 8 hours. After the reaction was finished, the reaction mixture was cooled to room temperature and neutralized with acetic acid. The reaction mixture was filtered, and the resulting solids were washed twice with 400 g isopropyl alcohol, and the resulting product was dried for 1 day at 60° C. under reduced pressure to give 48 g cellulose derivative having a polyoxyethylene cholesteryl ether group introduced into it.

30 g of the resulting cellulose derivative, 147 g isopropyl alcohol and 63 g ion exchange water were mixed and stirred at room temperature for 1 hour in a nitrogen stream. 2.56 g sodium chloroacetate and 3.67 g of 48% aqueous NaOH were added to the solution and stirred for 3 hours at 50° C. After stirring was finished, the reaction mixture was cooled to room temperature and neutralized with acetic acid. The reaction product was separated by filtration, and the resulting reaction product was washed twice with 180 g of 70% isopropyl alcohol and twice with 200 g isopropyl alcohol. The resulting cake was dried for 1 day under reduced pressure to give 30 g polyoxycholesterylated and carboxymethylated cellulose derivative. The degrees of substitution of the cholesteryl group and cation group of the resulting cellulose derivative were 0.0053 and 0.14, respectively.

The invention claimed is:

1. An allergen reducing method comprising spraying into the air an allergen-reducing agent comprising water and a water-soluble polymer compound having units having hydroxy or carboxy groups wherein at least a part of the hydrogen atoms of the hydroxy or carboxy groups are substituted by groups represented by the following formula (1):

$$—R^{1a}—(OR^{1b})_p\text{-}A\text{-}R^{1c} \quad (1)$$

wherein $R^{1a}$ is a group selected from the group consisting of an ethylene group, a propylene group, a trimethylene group, a 2-hydroxytrimethylene group, a 1-hydroxytrimethylene group, a 1-oxoethylene group, a 1-oxotrimethylene group and a 1-methyl-2-oxoethylene group, $R^{1b}$ is a group selected from the group consisting of an ethylene group and a propylene group, $R^{1c}$ is a group selected from the group consisting of a C5 to C25 alkyl group which may be substituted with a hydroxy group, A is —O—, p is a number of from 10 to 40 as the average number of moles added, and the groups ($OR^{1b}$) may be the same or different, wherein the air contains an allergen, wherein the water-soluble polymer compound is selected from the group consisting of hydroxyethyl cellulose, methyl cellulose, ethyl cellulose and hydroxypropyl cellulose.

2. The allergen-reducing method of claim 1, wherein said allergen-reducing agent is contained in a spray container provided with a spray device.

3. The allergen-reducing method according to claim 1, wherein water comprise 60-99.995 wt. % of said allergen-reducing agent.

4. The allergen-reducing method according to claim 1, wherein said allergen-reducing agent further comprises a water-soluble organic solvent.

5. The allergen-reducing method according to claim 4, wherein said water-soluble organic solvent forms an azeotropic mixture with water having an azeotropic point of lower than 100° C. with water at 1013.25 hPa.

6. The allergen-reducing method according to claim 4, wherein the amount of said water-soluble organic solvent is from 0.5 to 20 wt. %.

7. The allergen-reducing method according to claim 1, wherein said allergen-reducing agent further comprises a repellent against arthropods.

8. The allergen-reducing method according to claim 1, wherein the amount of said water-soluble polymer compound is from 0.005 to 10 wt. %.

9. The allergen-reducing method according to claim 1, wherein said water is substantially free from compounds which can act as allergens.

10. The allergen-reducing method according to claim 1, wherein said water is sterilized.

11. The allergen-reducing method according to claim 4, wherein said water-soluble organic solvent is at least one solvent selected from the group consisting of ethanol, cyclohexane, 2-butanol, cyclohexanol, cyclohexanone, cyclohexane, toluene, 1-butanol, 1-propanol, 2-propanol, 1-hexanol, hexane, 1-heptanol, 1-pentanol and 2-pentanol.

12. The allergen-reducing method according to claim 7, wherein the amount of said repellent against arthropods is from 0.001 to 2 wt. %.

13. The allergen-reducing method according to claim 1, wherein said allergen-reducing agent further comprises a sterilizing agent.

14. The allergen-reducing method according to claim 13, wherein said sterilizing agent is an antibacterial agent.

15. The allergen-reducing method according to claim 1, wherein said air is a household environment.

* * * * *